US005985564A

United States Patent [19]
Potter et al.

[11] Patent Number: 5,985,564
[45] Date of Patent: Nov. 16, 1999

[54] ASSAY FOR IDENTIFYING AGENTS THAT INHIBIT CHROMOSOME NON-DISJUNCTION

[75] Inventors: Huntington Potter, Boston; Jinhe Li, Cambridge, both of Mass.

[73] Assignee: President and Fellows of Harvard College, Cambridge, Mass.

[21] Appl. No.: 08/875,972

[22] PCT Filed: Aug. 15, 1996

[86] PCT No.: PCT/US96/13314

§ 371 Date: Aug. 8, 1997

§ 102(e) Date: Aug. 8, 1997

[87] PCT Pub. No.: WO97/07213

PCT Pub. Date: Feb. 27, 1997

Related U.S. Application Data XX.

[60] Provisional application No. 60/002,448, Aug. 16, 1995.

[51] Int. Cl.[6] ............................ C12Q 1/68; C12N 15/81; C12N 15/85; C07A 21/04
[52] U.S. Cl. .......................... 435/6; 435/69.1; 435/254.2; 435/254.21; 435/320.1; 435/325; 435/366; 435/372; 536/23.5
[58] Field of Search .............................. 435/6, 69.1, 366, 435/372, 325, 255.2, 320.1, 254.2, 254.21; 536/23.5, 24.31

[56] References Cited

FOREIGN PATENT DOCUMENTS

WO90/09452  8/1990  WIPO.
WO96/34099  10/1996 WIPO.
WO97/03192  1/1997  WIPO.

OTHER PUBLICATIONS

Gerring et al., The CHL 1(CTF1) gene product of Saccharomyces cerevisiae is important for chromosome transmission and normal cell cycle progression in G2/M, EMBO J. 9(13), 4347–4358, (Dec. 27, 1990).
McGrew et al., Saccharomyces cerevisiae Mutants Defective in Chromosome Segregation, Yeast 5, 271–284, (1989).
Williams et al., The Drosophila l(1)zw10 Gene Product, Required for Accurate Mitotic Chromosome Segregation, Is Redistributed at Anaphase Onset, J. Cell Biol. 118(4), Aug. 18, 1992.
Francisco et al., Type 1 Protein Phosphatase Acts in Opposition to lpl1 Protein Kinase in Regulating Yeast Chromosome Segregation, Molec Cell Biol. 14(7), 4731–4740 (Jun. 28, 1994).
Payne et al., A Mutation in PLC1, a Candidate Phosphoinositide–Specific Phospholipase C Gene from Saccharomyces cerevisiae, Causes Aberrant Mitotic Chromosome Segregation, Molec Cell Biol. 13(7), 4351–4364, (Jun. 25, 1993).
Allshire et al., A Fission Yeast Chromosome Can Replicate Autonomously in Mouse Cells, Cell 50, 391–403 (1987).
Polynucleotide Sequence Corresponding to Accession No. Z73986 submitted to GeneBank on Jun. 10, 1996.
Polynucleotide Sequence Corresponding to Accession No. D10495 D90470, submitted to GeneBank on Aug. 26, 1991.
R. Sherrington et al., "Cloning of a Gene Bearing Missense Mutations in Early–Onset Familial Alzheimer's Disease" *Nature* 375(*6534*): 754–760 (Jun. 29, 1995).
M. Wick et al., "Identification of Serum–Inducible Genes: Different Patterns of Gene Regulation During Go—S an G1—S Progression," *J Cell Science*, 107:227–239 (1994).
P. Buono et al., "The Complete Nucleotide Sequence of the Gene Coding for the Human Aldolase C," *Nucleic Acids Research*, 16(10):4733–4736 (May 25, 1988).
N. Tomita et al., "Transcription of Human Endogeneous Retroviral Long Terminal Repeat (LTR) Sequence in a Lung Cancer Cell Line," *Biochem. and Biophys. Res. Communications*, 166(1):1–10 (Jan. 15, 1990).
S. Stoler et al., "A Mutation in CSE4, an Essential Gene Encoding a Novel Chromatin–Associated Protein in Yeast, Causes Chromosome Nondisjunction and Cell Cycle Arrest at Mitosis," *Genes&Development* 9(5):573–586 (Mar. 1, 1995).
D. Koshland and P. Hieter, "Visual Assay for Chromosome Ploidy," *Methods in Enzymology*, 155:351–372 (1987).
P. Heiter et al., "Mitotic Stability od Yeast Chromosomes: A Colony Color Assay that Measures Nondisjunction and Chromosome Loss," *Cell*, 40(2):381–392 (Feb. 1985).
L. Levy–Lahad et al., "Candidate Gene for the Chromosome 1 Familial Alzheimer's Disease Locus," *Science*, 269:973–977 (Aug. 18, 1995).
E. I. Rogaev et al., "Familiar Alzheimler's Disease in Kindreds with Missense Mutations in a Gene on Chromosome 1 Related to the Alzheimer's Disease Type 3 Gene," *Nature*, 376:775–778 (Aug. 31, 1995).
J. Li, et al., "Identification and Expression Analysis of a Potential Familiar Alzheimer's Disease Gene on Chromosome 1 Related to AD3," *Proceedings of the National Academy of Sciences of U.S.A.*, 92(12):12180–12184 (Dec. 23, 1995).

(List continued on next page.)

*Primary Examiner*—John L. LeGuyader
*Assistant Examiner*—Mark L. Shibuya
*Attorney, Agent, or Firm*—Hamilton, Brook, Smith & Reynolds, P.C.

[57]        ABSTRACT

Disclosed is a method of identifying genes whose gene products cause chromosome missegregation. The method involves transfecting a mammalian gene being assessed into a cell and then assessing whether the progeny cells have increased aneuploidy or increased chromosome breaks or translocations compared with cells that have not been transfected with the gene. Genes identified in this manner are likely to be involved in causing diseases such as cancer and Alzheimer's Disease, which result from improper chromosome segregation. Also disclosed is a method of identifying agents which can be used in the treatment of diseases caused by improper chromosome segregation. The method involves treating cells that have been transfected with a gene whose gene product causes improper chromosome segregation with an agent being assessed. Cells showing less aneuploidy or less chromosomal breakage or translocation compared with untreated cells indicate that the agent is useful in the treatment of diseases caused by improper chromosome segregation.

12 Claims, 17 Drawing Sheets

OTHER PUBLICATIONS

R. Wilson et al., "2.2 Mb of Contiguous Nucleotide Sequence from Chromosome III of *C. elegans*," *Nature*, 368:32–38 (Mar. 3, 1994).

I. C. Eperon, et al., "Distinctive Sequence of Human Mitochondrial Ribosomal RNA Gene," *Nature*, 286(5772):460–467 (1980).

U. M. Wewer, et al., "Altered Levels of Laminin Receptor mRNA in Various Human Carcinoma Cells that have Different Abilities to Bind Laminin," *Proc. Natl. Acad. Sci. U.S.A.*, 83:7137–7141 (1986).

J. Girdlestone, and C. Milstein, "Differential Expression and Interferon Response of HLA Class I Genes in Thymocyte Lines and Response Variants," *Eur. J. Immunol.*, 18(1):139–143 (1988).

J. E. Brenman, et al., "Interaction of Nitric Oxide Synthase with the Postsynaptic Density Protein PSD–95 and Alpha1–Syntrophin Mediated by PDZ Domains," *Cell*, 84:757–767 (1996).

B. Van Hille, et al., "Heterogeneity of Vacuolar H+–ATPase: Differential Expression of Two Human Subunit B Isoform," *Biochem. J. 303*:191 (1994).

R. Hu, et al., "A Novel Human Homologue of Yeast Nucleosome Assembly Protein, 65 kb Centromeric to the p57KIP2 Gene, is Biallelically Expressed in Fetal and Adult Tissues," *Hum. Mol. Genet.*, 5:1743–1748 (1996).

F. W. Tsui and L. Siminovitch, "Isolation Structure and Expression of Mammalian Genes for Histidyl–tRNA Synthetase," *Nucleic Acids Res.*, 15:(8)3349–3367 (1987).

Polynucleotide Sequence Corresponding to Accession No. Z92817, submitted to GeneBank on Sep. 12, 1997.

Polynucleotide Sequence Corresponding to Accession No.__X95648, submitted to GeneBank on Feb. 13, 1996.

Polynucleotide Sequence Corresponding to Accession No. L32559, submitted to GeneBank on May 18, 1994.

```
AD4/AD3LP  1 GAGAATTCCCTTGCGGCCGACAGGCCTGGAGGAAGAGCTGACCCTCAAATACGGAGCGAA 60
             R  I  P  L  R  P  T  G  L  E  E  E  L  T  L  K  Y  G  A  K -
                                     |  |  |  |  |  |  |  |  |  |  |
             Q  V  V  E  Q  D  E  E  E  D  E  E  L  T  L  K  Y  G  A  K -
AD3      428 GCAGGTGGTGGAGCAAGATGAGGAAGAAGATGAGGAGCTGACATTGAAATATGGCGCCAA 487

61 GCACGTGATCATGCTGTGTGTGCCTGTCACTCTGTGCATGATCGTGGTGGTAGCCACCAT 120
             H  V  I  M  L  C  V  P  V  T  L  C  M  I  V  V  V  A  T  I -
             |  |  |  |  |     |  |  |  |  |  |  |  |  |  |  |  |  |  |
             H  V  I  M  L  F  V  P  V  T  L  C  M  V  V  V  V  A  T  I -
         488 GCATGTGATCATGCTCTTTGTCCCTGTGACTCTCTGCATGGTGGTGGTCGTGGCTACCAT 547

121 CAAGTCTGTGCGCTTCTACACAGAGAAGAATGGACAGCTCATCTACACGCCATTCACTGA 180
             K  S  V  R  F  Y  T  E  K  N  G  Q  L  I  Y  T  P  F  T  E -
             |  |  |     |  |  |        |  |  |  |  |  |  |  |  |  |
             K  S  V  S  F  Y  T  R  K  D  G  Q  L  I  Y  T  P  F  T  E -
         548 TAAGTCAGTCAGCTTTTATACCCGGAAGGATGGGCAGCTAATCTATACCCCATTCACAGA 607

181 GGACACACCCTCGGTGGGCCAGCGCCTCCTCAACTCCGTGCTGAACACCCTCATCATGAT 240
             D  T  P  S  V  G  Q  R  L  L  N  S  V  L  N  T  L  I  M  I -
             |  |     |  |  |  |  |                             |  |  |
             D  T  E  T  V  G  Q  R  A  L  H  S  I  L  N  A  A  I  M  I -
         608 AGATACCGAGACTGTGGGCCAGAGAGCCCTGCACTCAATTCTGAATGCTGCCATCATGAT 667

241 CAGCGTCATCGTGGTTATGACCATCTTCTTGGTGGTGCTCTACAAGTACCGCTGCTACAA 300
             S  V  I  V  V  M  T  I  F  L  V  V  L  Y  K  Y  R  C  Y  K -
             |  |  |  |  |  |  |     |  |  |  |  |  |  |  |  |  |  |
             S  V  I  V  V  M  T  I  L  L  V  V  L  Y  K  Y  R  C  Y  K -
         668 CAGTGTCATTGTTGTCATGACTATCCTCCTGGTGGTTCTGTATAAATACAGGTGCTATAA 747
                                        L

301 GTTCATCCATGGGTGGTTGATCATGTCTTCACTGATGCTGCTGTTCCTCTTCACCTATAT 360
             F  I  H  G  W  L  I  M  S  S  L  M  L  L  F  L  F  T  Y  I -
             |  |     |  |     |  |     |  |  |     |  |     |     |
             V  I  H  A  W  L  I  I  S  S  L  L  L  L  F  F  F  S  F  I -
         748 GGTCATCCATGCCTGGCTTATTATATCATCTCTATTGTTGCTGTTCTTTTTTTCATTCAT 807
                                R

361 CTACCTTGGGGAAGTGCTCAAGACCTACAATGTGGCCATGGACTACCCCACCCTCTTGCT 420
             Y  L  G  E  V  L  K  T  Y  N  V  A  M  D  Y  P  T  L  L  L -
             |  |  |  |  |     |  |  |  |  |  |     |  |  |  |  |
             Y  L  G  E  V  F  K  T  Y  N  V  A  V  D  Y  I  T  V  A  L -
         808 TTACTTGGGGGAAGTGTTTAAAACCTATAACGTTGCTGTGGACTACATTACTGTTGCACT 867

421 GACTGTCTGGAACTTCGGGGCAGTGGGGCATGGTGTGATCCACTGGAAGGGCCCTCTGGT 480
             T  V  W  N  F  G  A  V  G  H  G  V  I  H  W  K  G  P  L  V -
                   |  |  |  |     |  |     |           |  |  |  |  |
             L  I  W  N  F  G  V  V  G  M  I  S  I  H  W  K  G  P  L  R -
         868 CCTGATCTGGAATTTTGGTGTGGTGGGAATGATTTCCATTCACTGGAAAGGTCCACTTCG 927
```

Figure 1A

```
481 GCTGGAGCAGGCCTACCTCATCATGATCAGTGCGCTCATGCCCCTAATGTTCATCAAGTA 540
     L  E  Q  A  Y  L  I  M  I  S  A  L  M  P  L  M  F  I  K  Y  -
     |  |  |  |  |  |  |  |  |  |  |  |     |     |  |  |  |
     L  Q  Q  A  Y  L  I  M  I  S  A  L  M  A  L  V  F  I  K  Y  -
928 ACTCCAGCAGGCATATCTCATTATGATTAGTGCCCTCATGGCCCTGGTGTTTATCAAGTA 987

541 CCCTCCAGAGTGGTCCGCGTGGGTGATCCTGGCGCCCATCTCTGTGTATGATCTCGTGAC 600
     P  P  E  W  S  A  W  V  I  L  A  P  I  S  V  V  Y  D  L  V  T  -
     |  |  |     |     |  |     |  |  |  |  |  |  |  |  |  |  |
     L  P  E  W  T  A  W  L  I  L  A  V  I  S  V  Y  D  L  V  A  -
988 CCTCCCTGAATGGACTGCGTGGCTCATCTTGGCTGTGATTTCAGTATATGATTTAGTGGC 1047
                        E

601 TGTCCTGTGTTCCACAGGGCCTCTGAGAATGCTGGTAGAAACTGCCCAGGAGAGAAATGA 660
     V  L  C  S  T  G  P  L  R  M  L  V  E  T  A  Q  E  R  N  E  -
     |  |  |     |  |  |  |  |  |  |  |  |  |  |  |  |  |  |  |
     V  L  C  P  K  G  P  L  R  M  L  V  E  T  A  Q  E  R  N  E  -
1048 TGTTTTGTGTCCGAAAGGTCCACTTCGTATGCTGGTTGAAACAGCTCAGGAGAGAAATGA 1107

661 GACCATATTCTCTCCCCTGATATACTCATCTCCCATGGTGTGGACGGTTGTCATGTCGAA 720
     T  I  F  S  P  L  I  Y  S  S  P  M  V  W  T  V  V  M  S  K  -
     |  |  |        |  |  |  |     |  |  |  |     |     |
     T  L  F  P  A  L  I  Y  S  S  T  M  V  W  L  V  N  M  A  E  -
1108 AACGCTTTTTCCAGCTCTCATTTACTCCTCAACAATGGTGTGGTTGGTGAATATGGCAGA 1167
                       V

721 GCTGGACCCCTCCTCTCAGGGTGCCCTCCAGCTCCCCTACGACCCGGAGATGGAAGACTC 780
     L  D  P  S  S  Q  G  A  L  Q  L  P  Y  D  P  E  M  E  D  S  -
     |  |     |        |
     G  D  P  E  A  Q  R  R  V  S  K  N  S  K  Y  N  A  E  S  T  -
1168 AGGAGACCCGGAAGCTCAAAGGAGAGTATCCAAAAATTCCAAGTATAATGCAGAAAGCAC 1227

781 CTATGACAGTTTTGGGGAGCCTTCATACCCCGAAGTCTTTGAGCCTCCCCTGGCTGGCTA 840
     Y  D  S  F  G  E  P  S  Y  P  E  V  F  E  P  P  L  A  G  Y  -

E  R  E  S  Q  D  T  V  A  E  N  D  D  G  G  F  S  E  E  W  -
1228 AGAAAGGGAGTCACAAGACACTGTTGCAGAGAATGATGATGGCGGGTTCAGTGAGGAATG 1287

841 CCCAGGGGAGGAGCTGGAGGAAGAGGAGGAAAGTCAAGGG.................... 
     P  G  E  E  L  E  E  E  E  E  S  Q  G

E  A  Q  R  D  S  H  L  G  P  H  R  S  T  P  E  S  R  A  A  -
1288 GGAAGCCCAGAGGGACAGTCATCTAGGGCCTCATCGCTCTACACCTGAGTCACGAGCTGC 1347

...............................................GGCGTGAAG 889
                                                    G  V  K  -
                                                    |  |  |
     V  Q  E  L  S  S  S  I  L  A  G  E  D  P  E  E  R  G  V  K  -
1348 TGTCCAGGAACTTTCCAGCAGTATCCTCGCTGGTGAAGACCCAGAGGAAAGGGGAGTAAA 1407
```

Figure 1B

```
 890 CTTGTCCTCGGGACTTCAACTTCCACAGTTGTTCCTGGTGGCCAAGCGCCTCCCACGGGC 949
     L  V  L  G  T  S  T  S  T  V  V  P  G  G  Q  A  P  P  T  G
     |  |  |  |        |           |        |     |  |  |     |
     L  G  L  G  D  F  I  F  Y  S  V  L  V  G  K  A  S  A  T  A
1408 ACTTGGATTGGGAGATTTCATTTTCTACAGTGTTCTGGTTGGTAAAGCCTCAGCAACAGC 1467

950 AGCGGGGACTGGATAACCACGCTGGCCTGCTTCGTGGCCATCCTCATTGGCTTGTGTCTG 1009
     S  G  D  W  I  T  T  L  A  C  F  V  A  I  L  I  G  L  C  L  -
     |  |  |  |     |  |  |  |  |  |  |  |  |  |  |  |  |  |  |
     S  G  D  W  N  T  T  I  A  C  F  V  A  I  L  I  G  L  C  L  -
1468 CAGTGGAGACTGGAACACAACCATAGCCTGTTTCGTAGCCATATTAATTGGTTTGTGCCT 1527
                                  Y

1010 ACCCTCCTGCTGCTTGCTGTGTTCAAGAAGGCGCTGCCCGCCCTCCCCATCTCCATCACG 1069
     T  L  L  L  A  V  F  K  K  A  L  P  A  L  P  I  S  I  T  -
     |  |  |  |     |  |  |  |  |  |  |  |  |  |  |  |  |  |
     T  L  L  L  A  I  F  K  K  A  L  P  A  L  P  I  S  I  T  -
1528 TACATTATTACTCCTTGCCATTTTCAAGAAAGCATTGCCAGCTCTTCCAATCTCCATCAC 1567

1070 TTCGGGCTCATCTTTTACTTCTCCACGGACAGGAAGCACAGCAGGTTTATCCAGATGAAC 1129
     F  G  L  I  F  Y  F  S  T  D  R  K  H  S  R  F  I  Q  M  N  -
     |  |  |     |  |     |     |              |
     F  G  L  V  F  Y  F  A  T  D  Y  L  V  Q  P  F  M  D  Q  L  -
1568 CTTTGGGCTTGTTTTCTACTTTGCCACAGATTATCTTGTACAGCCTTTTATGGACCAATT 1627

1130 TGAGAAGGTCAGATTAGGGCGGGGAGAAGAGCATCCGGCATGAGGGCTGAGATGCGCAAA 1189
     *

A  F  H  Q  F  Y  I  *
1628 AGCATTCCATCAATTTTATATCTAGCATATTTGCGGTTAGAATCCCATGGATGTTTCTTC 1687

1190 GAGTGTGCTCGGGAGTGGCCCCTGGCACCTGGGTGCTCTGGCTGGAGAGGAAAAACCAGT 1249
1688 TTTGACTATAACCAAATCTGGGGAGGACAAAGGTGATTTTCCTGTGTCCACATCTAACAA 1747

1250 TCCCTACGAGGAGTGTTCCCAATGCTTTGTCCATGATGTCCTTGTTATTTTATTGCCTTT 1309
1748 AGTCAAGATTCCCGGCTGGACTTTTGCAGCTTCCTTCCAAGTCTTCCTGACCACCTTGCA 1807

1310 AGAAACTGAGTCCTGTTCTTGTTACGGCAGTCACACTGCTGGGAAGTGGCTTAATACTAA 1369
1808 CTATTGGACTTTGGAAGGAGGTGCCTATAGAAAACGATTTTGAACATACTTCATCGCAGT 1867

1370 TATCAATAAATAGATGAGTCCTGTTAGAAAAAAAAAAAAAAAAAAAA 1417
1868 GGACTGTGTCCCTCGGTGCAGAAACTACCAGATTTGAGGGACGAGGTC 1915
```

Figure 1C

```
  1 CTATACGAAG XGCAGAGAAA TAAGGCCTAC TTCACAAGCG CCTTCCCCCG
 51 TAATGATATC ATCTCAACTT AGTATTATAC CCACACCCAC CCAAGAATAG
101 GGTTTAAAAA
```
Figure 4

```
  1 CTCTATTGGT CTGAACTGTT CTTTCACGTT TCCCATTTCC CTGTGGCTCA
 51 CTGTGCTTAC AATCACTGCT GTGGAATCAT GATACCACTT TTAGCTCTTT
101 GTATCTTCCT TCAGTGTATT TTTGTTTTTC AAGAGTAAGT AGATTTTAAC
151 TGGACAACTT TGAGTACTGA CATCATTGAT AAATAAACTG GCTTGTGGTT
201 TCAATAAAAA
```
Figure 5

```
  1 CACACCCGAG CAAAACTGTT TATTCTTGAG AAGTTCCATC TTCATTTCTG
 51 CCACAGTTGG AACTTCCCGA GGAAGGAAGG AGGCCTGAGG TTTTGCACAA
101 TCTGTTTCAG AGCCTGTTTA GACTCAAACC TATGCTTCCC TTGGCAGCAG
151 AATACACTTA ACCTAAAGCA GTATTGGAG TTGAGAAAAA CCTGGTGGGG
201 TAAGTGAATA TGTACTGTTT GGTAGGGTAG GTAGAGAAGC TGTGCTTTGA
251 CCCTGTGATT CCATCTTTTT CTACCTTCTA TGATGGTGAT GAAGCTAGAT
301 ACCCCTAGGG AAGAAAGAAG GACTGGGTTT AGCAAAAATG ATTTGGTAAA
351 TAAAGTTTAT TTGAACACAA AAA
```
Figure 6

```
  1 CTGAGGACCT TTTGTCTGAG AATCAGTAGT GTTTTAAGGT GCTGATATCG
 51 AATTAATGAA GTAAAGTTGT TGATGGTGGT GAAACACCGT AGGGCATGTG
101 GTTCAAAGAG AAGCAGGAGG GCAAGGGAAA GTTACCCTGA TCTTAGTTTG
151 TAGCTTATGA CTTATTTAAT GAATGGATGC CCAGCCAAGC TCAGAGTAGG
201 CGCCCAAAGC ATTGTGGAGT AGTTCCTGT TTTGTCTTTT TTTTTTTTT
251 TTTTTAAGCC ATGACATCCC AGAAGAGGAC AGTGAATTAC TCCTAGGTCG
301 GCTCTTATAG AGTGGCCATA GTGTTCTGTC AAAACACTTG CTTCCATTTT
351 CAGAGATAAA AATCATTGAT TACAAAAA
```
Figure 7

```
  1  TCAGGTGATG  ACCGTCCGCT  CCTAGTTCAC  TGCTAGCTCA  GCCTGAGGTT
 51  GCAGACTGGT  CTGAAGGTGT  ACAGGTGCCC  TCTGTGCCTA  TTCAGCAATT
101  CCCTACTGAA  GACTGGAGCG  CTCAGCCTGC  CACGAACTGG  ACTGCAGCTC
151  CACTGCTCAG  GCCAACTGAA  TGGGTAGGAG  CAACCACTGA  CTGGTCTAAG
201  CTGTTCTTGC  ATAGGCTCTT  AAGCAGCATG  GAAAAATGGT  TGATGGAAGA
251  TAAACATCAG  TTTCTAAAAA
```

Fig. 8

1   AGTTCTAAGG CTGCTGCTAA TTACAXXXXX XXXXXXXXXX GCTGACCTAG
51  AAGCAGCACC ATTCCCATTT CCTCAGTACC CACAAAGTGC AGCCCACATT
101 GGAGCCCCAG ACACCCCTCT GCAGCCATTG ACTGCAACTT GTTCTTTTGC
151 CCATTAAAAA

Fig. 9

```
  1  AAGAGAGTGA AACAGCCACC TGTGTCACTG TGCCCGTCCA TGCTGACCTG
 51  TGTTCCTCCC CAGTCTCTTC TTGTTCCAGA GAGGTGGGGC TGATGTCTCC
101  ATCTCTGTCT CACTTTATGT GCACTGAGCT GCAACTTCTT ACTTCCCTAC
151  TGAAAATAGA TCTGAATACG ATTGTTTCTC AATATTGCTA TGAGAGGTTG
201  ATGATTAATT AAATAAGTCA ATTCCTGGAA GTGAGAGAGC AAATAAAGAC
251  CTGAGAACCT TCCAGAAAAA
```

Figure 10

```
  1  TCGCAGATAC AGCTGTCAGG CTGCCTCCTG CCTTTTCTTT TGTAAAGACA
 51  AGACCCTTGG AGTTTTAATT CTGTTTTGTA CTTCCTGTGG GGCCTCCACT
101  GCTTTTCTAT GGGAGACACT CTTAATTTAA CAGATGTGTA TATTTTGAAA
151  CTCTGAAAAA
```

Figure 11

```
  1  GTCAGTTCGA TCGGCTCTAG TAGCCTGAGC ACTCATGCAG TCGCATGGCT
 51  CTGTGTCTCT CTGGTCTTGT ACTTGGTGCA ATAGCAACTT CCCTACCCGT
101  GCATTCCATC TTTCATGTTG TGTAAAGTTC TTCACTTTTT TCTCTGAGGG
151  CTGGGGGTTG GGGGAGTCAG CATGATTATA TTTTAATGTA GAAAATGTGA
201  CATCTGGATA TAAAATGAAG ATAAATGTTA AATTAAATGG ACCTTAAAAA
```
Figure 12

```
  1  AAGTGTATCT TACTGTGCCT GTCAGGTTAC AAACTAGTGC GTTGACGCAC
 51  AGTGTCCAAG TTATTAGAGC CCTTGTTAGC CAGACCCAGG TGTCCTGGTC
101  ACCGTTTCAC CATCATGCTT TGATGTTCCC CTGTCTTTCC CTCTTCTGCT
151  CTCAAGAGCA AAGGTTAATT AAGGTGCAAA GATGAAGTCA CTGTAAACTA
201  ATCTGTCATT GTTTTGCCT TCCTTTTCTT TTTCAGTGCA GAAATTAAAA
251  GTAAGTATAA AGCACAAAAA
```
Figure 13

```
  1  TTGCAAGAAG TCAGAACNGG ATGGCTGGGT CTCCCCCTAC CTCTTCCAGC
 51  TCCCACAATT TTNCCATGAT GAGGTAGCTT CTCCCTGGGC TCTCCTTCTT
101  GCCTACCCTG TCTCCTGGGA TCAGAGGGTA GTACAGAAGC CCTGACTCAT
151  GCCTTGAGTA CATACCATAC AGCAAATAAN TGGTAGCAAA ACATTAAAAA
```
Figure 14

```
  1  AAGGAAGTGA AATCAAAGAC AGGCAGCCCG GCACCAGGCC TGAAACCAGC
 51  CCTGGGCCTG CCTGGCCTAA AGCTAGTAGT TAAAAATCAA CTTACGACTT
101  AGAACCTGAT GTTATCCGTA GATTCCAAGC ATTGTATAAA AAAATTGTGA
151  AACTCCCTGT TGTGTTCTGT ACCAGTGCAT GAAACCCCTG TCACATATCC
201  CCTAGATTGC TCAATCAATC NCGACCCTTT CATGTGAAAT CTTTAGTGTT
251  GTGAGCCCTN AAAAGGGACA GAAATTGTGC ACTTGAGGAG CTCAGATTTT
301  AAGGCTGTAG CTTGCCGATG CTCCCAGCTG AATAAAGCCC TTCCTTCNAC
351  AACTCTGAAA AA
```
Figure 15

```
  1  ACCATGGATT CATGGTTTAT TTTATTCAGT GAGTTATAAT TCATTAATAT
 51  TGTTATTAAA AATTTGTTTT TCTTTTAAGA AATGTTATAT TTTGACAACT
101  TCAGACTTAC AGAAAGATTA TAAGAGGTAG NNCAAATAAT TTTTGGATAT
151  TATTCCCCAA ATGTTAACAT TTTACTGCAT TTACTTTATC CTTTCTCCCC
201  CTTCTCCTCC TGTCTTTCTA GATGAATATG AATATAGGTA CTTAATACAG
251  ATTTTTTTTC TAAACTGTTT GTAGGTTGCA GACACGATGC CTCTTTATTT
301  CTAAATAATG TGTATTTCCT AAATAAAAGG AATTACCTTA AAAA
```

Figure 16

```
  1  GTGACTGTGT ACTCTGCTGC TGCCGCCCTG CCCCAGAGCT CTCCTTGGCT
 51  GCGTCTGGCC GGCTCTCATG GTACTTCCTC TGTGAACTGT GTGTGAATCT
101  GCTTTTCCTC TGCTTCGGAG GAAATTGTAA ATCCTGTGTT TCATTACTTG
151  AATGTAGTTA TCTATTGAAA ATATATATTA TATACATAGA CATATATATA
201  TATATAAAAA
```

Figure 17

```
  1  ACTCGATCTC TCACTAGACT GGCTGAAGTC CTACGTTCAG TGAAGATAAC
 51  TAAGTCCTGC TTTCTCAGTA CGCATTGCGG GTTTTACCAT TCATCCTGTC
101  TAAGGTCCTG GGTTTGGTGT GAGCTTGGCG GCTGGTGGGT GGGGTTTTCA
151  AGTGGGTCAC GGCGCTCTCG GCAGCCGGGG ATGCGTGTCC GCACTGACAG
201  CCTGTGAGAG TGCTCGGCCT AACCTTAGAA CACATTGTAA CTGAATACAG
251  TGTTTTCAAT TTGTACAGAA TAGTTAGNAT ATTCTATTAA AGTGGTGAAA
301  CATTGAAAAA
```

Figure 18

```
  1  GGGGCACCCT CCCTGGCCAC ACGCCTGTTC CCAGCAAGTG CTGAAACTCA
 51  CTAGACCGTC TGCCTGTTTC GAAATGGGGA AAGCCGTGCG TGCGCGTTAT
101  TTATTTAAGT GCGCCTGTGT GCGCGGGTGT GGGAGCACAC TTTGCAAAGC
151  CACAGCGTTT CTGGTTTTGG GTGTACAGTC TTGTGTGCCT GGCGAGAAGA
201  ATATTTTCTA TTTTTTTAAG TCATTTCATG TTTCTGTCTG GGGAAGGCAA
251  GTTAGTTAAG TATCACTGAT GTGGGTTGAG ACCAGCACTC TGTGAAACCT
301  TGAAATGAGA AGTAAAGGCA GATGAAAAGA AAGAAAA
```

Figure 19

```
  1 TCTACTCGAA ACGCAGTACA CACTTTATCA GCCAGAGCTA GTCAGTCTGT
 51 GCTCCTGGCT ATAAGACCCA GCCTGAGATG GTCCCATCTG CAGGGCCCGC
101 ACCAGTTGGA CAGATGCCTC CCCACCACCA ATTGCCAAAG GTCCAATAAA
151 ATGCCTCAAC CACGGAAAAA
```
Figure 20

```
  1 CTGCCAGTTT CAGGCCTCGG TCCATAGAGA CACCACCACC ATGGCCAGTG
 51 AAAGGTATAG TCCTGCAGCA GCTGTCTCCT GGTGCAGGTG CCTGCCAGCC
101 CACTGGATTG GACGGGCCA GGCTGGGCCA GGTCGGGGGC TCAGTCTGGG
151 AGGTAATAAA AGCAGACCGA CACGCAAAA
```
Figure 21

```
  1 GGCAAGCAGX TTCTGGTGGG TGTGTGGTGG TACCTCACTG TGGTTTTGGT
 51 TTGCGTTTTC CTCTATTTGC ACAAAATGAT ATTAAATATA TTTTATGCTT
101 ATTAGTCATT
```
Figure 22

```
  1 CAGAAGGTCT GCCATGGAGT TGCAGTCATC ACGGTAGATG GCGTATGATT
 51 TTGCTGAATT TTAAATAAAA TGAAAACCAT AAATTAAAA
```
Figure 23

```
  1 TAAAATTTCG GTTGGGCGAC CTCGGAGCAG AACCAACCTC CGAGCAGTAC
 51 ATGCTAAGAC TTCACCAGTC AAAGCGAACT ACTATACTCA ATTGATCCAA
101 TAACTTGACC AACGGAACAA GTTACCCTAG GATAACAGC GCAATCCTAT
151 TCTAGAGTCC ATATCAACAA TAGGGTTTAC GACCTCGATG TTGGATCAGG
201 ACATCCCGAT GGTGCAGCCG CTATTAAAGG TTCGTTTGTT CAACGATTAA
251 AGTCCTACGT GATCTGAGTT CAGACCGGAG TAATCCAGGT CGGTTTCTAT
301 CTACTTCAAA TTCCTCCCTG TACGAAAGGA CAAGAGAAAT AAGGCCTACT
351 TCACAAAGCG CCTTCCCCGT AAATGATATC ATCTCAACTT AGTATTATAC
401 CCACACCCAC CCAAGAACAG GGTTTGTTAA AAA
```
Figure 24

```
  1  ATTACAATTC AGTTTCTGTG ACATCTTTTT AAACCACTGG AGGAAAAATG
 51  AGATATTCTC TAATTTATTC TTCTATAACA CTCTATATAG AGCTATGTGA
101  GTNCTAATCA CATTGAATAA TAGTTATAAA ATTATTGTAT AGACATCTGC
151  TTCTTAAACA GNTTGTGAGT TCTTTGAGAA ACAGCGTGGA TTTTACTTAT
201  CTGTGTATTC ACAGAGCTTA GCNCAGTGCC TGGTAATGAG CAAGCATACT
251  TGCCATTACT TTTCCTTCCC ACTCTCTCCA ACATCACATT CACTTTAAAT
301  TTTTCTGTAT ATAGAAAGGA AAACTAGCCT GGGCAACATG ATGAAACCCC
351  ATCTCCACTG CAAAAA
```

Figure 25

```
  1  TAAGTAGTAG AAGCTGTTAA TATACATGCA TCGTAACCTC AGAAGCAAGA
 51  GAATGTTTTG TGGACCACTT TGGTTTTCTT TTTTGCGTGT GGCAGTTTTA
101  AGTTATTAGT TTTTAAAATC AGTACTTTTT AATGGAAACA ACTTGACCAA
151  AAATTTGTCA CAGAATTTTG AGACCCATTA AAAAGTTAA ATGAGAAAAA
```

Figure 26

```
  1 CTCTACCGGA TCCACTATTA CGGGGGGGGG GGGGGGGGCT GGACCGCGGC
 51 GGCAGAAACA GGCATTTCCA GCAGTGAGGA GACAGCCAGA AGCAAGCTTT
101 TGGAGCTGAA GGAACCTGAG ACAGAAGCTA GTCCCCCCTC TGAATTTTAC
151 TGATGAAGAA ACTGAGGCCA CAGAGCTAAA GTGACTTTTC CCAAGGTCGC
201 CCAGCGAGGA CGTGGGACTT CTCAGACGTC AGGAGAGTGA TGTGAGGGAG
251 CTGTGTGACC ATAGAAAGTG ACGTGTTAAA AACCAGCGCT GCCCTCTTTG
301 AAAGCCAGGG AGCATCATTC ACTTAGCCTG CTGAGAAGAA GAAACCAAGT
351 GTCCGGGATT CAGACCTCTC TGCGGCCCCA AGTGTTCGTG GTGCTTCCAG
401 AGGCAGGGCT ATGCTCACAT TCATGGCCTC TGACAGCGAG GAAGAAGTGT
451 GTGATGAGCG GACGTCCCTA ATGTCGGCCG AGAGCCCCAC GCCGCGCTCC
501 TGCCAGGAGG GCAGGCAGGG CCCAGAGGAT GGAGAGAACA CTGCCCAGTG
551 GAGAAGCCAG GAGAACGAGG AGGACGGTGA GGAGGACCCT GACCGCTATG
601 TCTGTAGTGG GGTTCCCGGG CGGCCGCCAG GCCTGGAGGA AGAGCTGACC
651 CTCAAATACG GAGCGAAGCA CGTGATCATG CTGTTTGTGC CTGTCACTCT
701 GTGCATGATC GTGGTGGTAG CCACCATCAA GTCTGTGCGC TTCTACACAG
751 AGAAGAATGG ACAGCTCATC TACACGCCAT TCACTGAGGA CACACCCTCG
801 GTGGGCCAGC GCCTCCTCAA CTCCGTGCTG AACACCCTCA TCATGATCAG
851 CGTCATCGTG GTTATGACCA TCTTCTTGGT GGTGCTCTAC AAGTACCGCT
901 GCTACAAGTT CATCCATGGC TGGTTGATCA TGTCTTCACT GATGCTGCTG
951 TTCCTCTTCA CCTATATCTA CCTTGGGGAA GTGCTCAAGA CCTACAATGT
1001 GGCCATGGAC TACCCCACCC TCTTGCTGAC TGTCTGGAAC TTCGGGGCAG
1051 TGGGCATGGT GTGCATCCAC TGGAAGGGCC CTCTGGTGCT GCAGCAGGCC
1101 TACCTCATCA TGATCAGTGC GCTCATGGCC CTAGTGTTCA TCAAGTACCT
1151 CCCAGAGTGG TCCGCGTGGG TCATCCTGGG CGCCATCTCT GTGTATGATC
1201 TCGTGGCTGT GCTGTGTCCC AAAGGGCCTC TGAGAATGCT ggtagaaact
```

Figure 28A 1251 gcccaggaga gaaatgagcc catattccct gccctgatat actcatctgc 1301 catggtgtgg acggttggca tggcgaagct ggaccctcc tctcagggtg 1351 ccctccagct cccctacgac ccggagatgg aagactccta tgacagtttt 1401 ggggagcctt catacccga agtctttgag cctcccttga ctggctaccc 1451 aggggaggag ctggaggaag aggaggaaag gggcgtgaag cttggcctcg 1501 gggacttcat cttctacagt gtgctggtgg gcaaggcggc tgccacgggc 1551 agcggggact ggaataccac gctggcctgc ttcgtggcca tcctcattgg 1601 cttgtgtctg accctcctgc tgcttgctgt gttcaagaag gcgctgcccg 1651 ccctccccat ctccatcacg ttcgggctca tcttttactt ctccacggac 1701 aacctggtgc ggccgttcat ggacaccctg gcctcccatc agctctacat 1751 ctgagggaca tggtgtgcca caggctgcaa gctgcaggga attttcattg 1801 gatgcagttg tatagtttta cactctagtg ccatatattt ttaagacttt 1851 tctttcctta aaaaataaag tacgtgttta cttggtgagg aggaggcaga 1901 accagctctt tggtgccagc tgtttcatca ccagactttg gctcccgctt 1951 tggggagcgc ctcgcttcac ggacaggaag cacagcaggt ttatccagat 2001 gaactgagaa ggtcagatta gggcggggag aagagcatcc ggcatgaggg 2051 ctgagatgcg caaagagtgt gctcgggagt ggccctggc acctgggtgc 2101 tctggctgga gaggaaaagc cagttccta cgaggagtgt tcccaatgct 2151 ttgtccatga tgtccttgtt attttattgc ctttagaaac tgagtcctgt 2201 tcttgttacg gcagtcacac tgctgggaag tggcttaata gtaatatcaa 2251 taaatagatg agtcctgtta gaaaaa

Figure 28B

```
  1 MLTFMASDSE EEVCDERTSL MSAESPTPRS CQEGRQGPED GENTAQWRSQ
 51 ENEEDGEEDP DRYVCSGVPG RPPGLEEELT LKYGAKHVIM LFVPVTLCMI
101 VVVATIKSVR FYTEKNGQLI YTPFTEDTPS VGQRLLNSVL NTLIMISVIV
151 VMTIFLVVLY KYRCYKFIHG WLIMSSLMLL FLFTYIYLGE VLKTYNVAMD
201 YPTLLLTVWN FGAVGMVCIH WKGPLVLQQA YLIMISALMA LVFIKYLPEW
251 SAWVILGAIS VYDLVAVLCP KGPLRMLVET AQERNEPIFP ALIYSSAMVW
301 TVGMAKLDPS SQGALQLPYD PEMEDSYDSF GEPSYPEVFE PPLTGYPGEE
351 LEEEEERGVK LGLGDFIFYS VLVGKAAATG SGDWNTTLAC FVAILIGLCL
401 TLLLLAVFKK ALPALPISIT FGLIFYFSTD NLVRPFMDTL ASHQLYI
```

Figure 29

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
      (A) LENGTH: 1417 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 2..1129

(xi) SEQUENCE DESCRIPTION: SEQ ID NO:1:

```
G AGA ATT CCC TTG CGG CCG ACA GGC CTG GAG GAA GAG CTG ACC CTC         46
  Arg Ile Pro Leu Arg Pro Thr Gly Leu Glu Glu Glu Leu Thr Leu
    1               5                  10                  15

AAA TAC GGA GCG AAG CAC GTG ATC ATG CTG TGT GTG CCT GTC ACT CT       94
Lys Tyr Gly Ala Lys His Val Ile Met Leu Cys Val Pro Val Thr Leu
                 20                  25                  30

TGC ATG ATC GTG GTG GTA GCC ACC ATC AAG TCT GTG CGC TTC TAC ACA     142
Cys Met Ile Val Val Val Ala Thr Ile Lys Ser Val Arg Phe Tyr Thr
             35                  40                  45

GAG AAG AAT GGA CAG CTC ATC TAC ACG CCA TTC ACT GAG GAC ACA CCC     190
Glu Lys Asn Gly Gln Leu Ile Tyr Thr Pro Phe Thr Glu Asp Thr Pro
         50                  55                  60

TCG GTG GGC CAG CGC CTC CTC AAC TCC GTG CTG AAC ACC CTC ATC ATG     238
```

```
        Ser Val Gly Gln Arg Leu Leu Asn Ser Val Leu Asn Thr Leu Ile Met
                    65                  70                  75

ATC AGC GTC ATC GTG GTT ATG ACC ATC TTC TTG GTG GTG CTC TAC AAG         286
Ile Ser Val Ile Val Val Met Thr Ile Phe Leu Val Val Leu Tyr Lys
 80                  85                  90                  95

TAC CGC TGC TAC AAG TTC ATC CAT GGG TGG TTG ATC ATG TCT TCA CTG         334
Tyr Arg Cys Tyr Lys Phe Ile His Gly Trp Leu Ile Met Ser Ser Leu
                100                 105                 110

ATG CTG CTG TTC CTC TTC ACC TAT ATC TAC CTT GGG GAA GTG CTC AAG         382
Met Leu Leu Phe Leu Phe Thr Tyr Ile Tyr Leu Gly Glu Val Leu Lys
                    115                 120                 125

ACC TAC AAT GTG GCC ATG GAC TAC CCC ACC CTC TTG CTG ACT GTC TGG         430
Thr Tyr Asn Val Ala Met Asp Tyr Pro Thr Leu Leu Leu Thr Val Trp
            130                 135                 140

AAC TTC GGG GCA GTG GGG CAT GGT GTG ATC CAC TGG AAG GGC CCT CTG         478
Asn Phe Gly Ala Val Gly His Gly Val Ile His Trp Lys Gly Pro Leu
        145                 150                 155

GTG CTG GAG CAG GCC TAC CTC ATC ATG ATC AGT GCG CTC ATG CCC CTA         526
Val Leu Glu Gln Ala Tyr Leu Ile Met Ile Ser Ala Leu Met Pro Leu
160                 165                 170                 175

ATG TTC ATC AAG TAC CCT CCA GAG TGG TCC GCG TGG GTG ATC CTG GCG         574
Met Phe Ile Lys Tyr Pro Pro Glu Trp Ser Ala Trp Val Ile Leu Ala
                180                 185                 190

CCC ATC TCT GTG TAT GAT CTC GTG ACT GTC CTG TGT TCC ACA GGG CCT         622
Pro Ile Ser Val Tyr Asp Leu Val Thr Val Leu Cys Ser Thr Gly Pro
                    195                 200                 205

CTG AGA ATG CTG GTA GAA ACT GCC CAG GAG AGA AAT GAG ACC ATA TTC         670
Leu Arg Met Leu Val Glu Thr Ala Gln Glu Arg Asn Glu Thr Ile Phe
                210                 215                 220

TCT CCC CTG ATA TAC TCA TCT CCC ATG GTG TGG ACG GTT GTC ATG TCG         718
Ser Pro Leu Ile Tyr Ser Ser Pro Met Val Trp Thr Val Val Met Ser
225                 230                 235

AAG CTG GAC CCC TCC TCT CAG GGT GCC CTC CAG CTC CCC TAC GAC CCG         766
Lys Leu Asp Pro Ser Ser Gln Gly Ala Leu Gln Leu Pro Tyr Asp Pro
240                 245                 250                 255

GAG ATG GAA GAC TCC TAT GAC AGT TTT GGG GAG CCT TCA TAC CCC GAA         814
Glu Met Glu Asp Ser Tyr Asp Ser Phe Gly Glu Pro Ser Tyr Pro Glu
                260                 265                 270

GTC TTT GAG CCT CCC CTG GCT GGC TAC CCA GGG GAG GAG CTG GAG GAA         862
Val Phe Glu Pro Pro Leu Ala Gly Tyr Pro Gly Glu Glu Leu Glu Glu
                    275                 280                 285

GAG GAG GAA AGT CAA GGG GGC GTG AAG CTT GTC CTC GGG ACT TCA ACT         910
Glu Glu Glu Ser Gln Gly Gly Val Lys Leu Val Leu Gly Thr Ser Thr
                290                 295                 300

TCC ACA GTT GTT CCT GGT GGC CAA GCG CCT CCC ACG GGC AGC GGG GAC         958
Ser Thr Val Val Pro Gly Gly Gln Ala Pro Pro Thr Gly Ser Gly Asp
305                 310                 315

TGG ATA ACC ACG CTG GCC TGC TTC GTG GCC ATC CTC ATT GGC TTG TGT         1006
Trp Ile Thr Thr Leu Ala Cys Phe Val Ala Ile Leu Ile Gly Leu Cys
320                 325                 330                 335

CTG ACC CTC CTG CTG CTT GCT GTG TTC AAG AAG GCG CTG CCC GCC CTC         1054
Leu Thr Leu Leu Leu Leu Ala Val Phe Lys Lys Ala Leu Pro Ala Leu
                340                 345                 350

CCC ATC TCC ATC ACG TTC GGG CTC ATC TTT TAC TTC TCC ACG GAC AGG         1102
Pro Ile Ser Ile Thr Phe Gly Leu Ile Phe Tyr Phe Ser Thr Asp Arg
                355                 360                 365

AAG CAC AGC AGG TTT ATC CAG ATG AAC TGAGAAGGTC AGATTAGGGC               1149
Lys His Ser Arg Phe Ile Gln Met Asn
                370                 375

GGGGAGAAGA GCATCCGGCA TGAGGGCTGA GATGCGCAAA GAGTGTGCTC GGGAGTGGCC       1209
```

-continued

```
CCTGGCACCT GGGTGCTCTG GCTGGAGAGG AAAAACCAGT TCCCTACGAG GAGTGTTCCC    1269

AATGCTTTGT CCATGATGTC CTTGTTATTT TATTGCCTTT AGAAACTGAG TCCTGTTCTT    1329

GTTACGGCAG TCACACTGCT GGGAAGTGGC TTAATACTAA TATCAATAAA TAGATGAGTC    1389

CTGTTAGAAA AAAAAAAAAA AAAAAAA                                        1417
```

(2) INFORMATION FOR SEQ ID NO:2:

(i) SEQUENCE CHARACTERISTICS:
        (A) LENGTH: 376 amino acids
        (B) TYPE: amino acid
        (D) TOPOLOGY: linear (ii) MOLECULE TYPE: protein (xi) SEQUENCE DESCRIPTION: SEQ ID NO:2:

```
Arg Ile Pro Leu Arg Pro Thr Gly Leu Glu Glu Leu Thr Leu Lys
 1               5                  10                  15

Tyr Gly Ala Lys His Val Ile Met Leu Cys Val Pro Val Thr Leu Cys
                20                  25                  30

Met Ile Val Val Val Ala Thr Ile Lys Ser Val Arg Phe Tyr Thr Glu
                35                  40                  45

Lys Asn Gly Gln Leu Ile Tyr Thr Pro Phe Thr Glu Asp Thr Pro Ser
 50                  55                  60

Val Gly Gln Arg Leu Leu Asn Ser Val Leu Asn Thr Leu Ile Met Ile
 65                  70                  75                  80

Ser Val Ile Val Val Met Thr Ile Phe Leu Val Val Leu Tyr Lys Tyr
                85                  90                  95

Arg Cys Tyr Lys Phe Ile His Gly Trp Leu Ile Met Ser Ser Leu Met
                100                 105                 110

Leu Leu Phe Leu Phe Thr Tyr Ile Tyr Leu Gly Glu Val Leu Lys Thr
                115                 120                 125

Tyr Asn Val Ala Met Asp Tyr Pro Thr Leu Leu Leu Thr Val Trp Asn
                130                 135                 140

Phe Gly Ala Val Gly His Gly Val Ile His Trp Lys Gly Pro Leu Val
145                 150                 155                 160

Leu Glu Gln Ala Tyr Leu Ile Met Ile Ser Ala Leu Met Pro Leu Met
                165                 170                 175

Phe Ile Lys Tyr Pro Pro Glu Trp Ser Ala Trp Val Ile Leu Ala Pro
                180                 185                 190

Ile Ser Val Tyr Asp Leu Val Thr Val Leu Cys Ser Thr Gly Pro Leu
                195                 200                 205

Arg Met Leu Val Glu Thr Ala Gln Glu Arg Asn Glu Thr Ile Phe Ser
210                 215                 220

Pro Leu Ile Tyr Ser Ser Pro Met Val Trp Thr Val Met Ser Lys
225                 230                 235                 240

Leu Asp Pro Ser Ser Gln Gly Ala Leu Gln Leu Pro Tyr Asp Pro Glu
                245                 250                 255

Met Glu Asp Ser Tyr Asp Ser Phe Gly Glu Pro Ser Tyr Pro Glu Val
                260                 265                 270

Phe Glu Pro Pro Leu Ala Gly Tyr Pro Gly Glu Glu Leu Glu Glu Glu
                275                 280                 285

Glu Glu Ser Gln Gly Gly Val Lys Leu Val Leu Gly Thr Ser Thr Ser
                290                 295                 300

Thr Val Val Pro Gly Gly Gln Ala Pro Pro Thr Gly Ser Gly Asp Trp
305                 310                 315                 320
```

```
Ile Thr Thr Leu Ala Cys Phe Val Ala Ile Leu Ile Gly Leu Cys Leu
            325                 330                 335

Thr Leu Leu Leu Leu Ala Val Phe Lys Lys Ala Leu Pro Ala Leu Pro
            340                 345                 350

Ile Ser Ile Thr Phe Gly Leu Ile Phe Tyr Phe Ser Thr Asp Arg Lys
            355                 360                 365

His Ser Arg Phe Ile Gln Met Asn
    370                 375

(2) INFORMATION FOR SEQ ID NO:3:

(i) SEQUENCE CHARACTERISTICS:
        (A) LENGTH: 1488 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 2..1222

(xi) SEQUENCE DESCRIPTION: SEQ ID NO:3:
```

| | | | | | | | | | | | | | | | | |
|---|---|---|---|---|---|---|---|---|---|---|---|---|---|---|---|---|
| G | CAG | GTG | GTG | GAG | CAA | GAT | GAG | GAA | GAA | GAT | GAG | GAG | CTG | ACA | TTG | 46 |
| | Gln | Val | Val | Glu | Gln | Asp | Glu | Glu | Glu | Asp | Glu | Glu | Leu | Thr | Leu | |
| | 1 | | | 5 | | | | | 10 | | | | | 15 | | |

```
AAA TAT GGC GCC AAG CAT GTG ATC ATG CTC TTT GTC CCT GTG ACT CTC    94
Lys Tyr Gly Ala Lys His Val Ile Met Leu Phe Val Pro Val Thr Leu
            20                  25                  30

TGC ATG GTG GTG GTC GTG GCT ACC ATT AAG TCA GTC AGC TTT TAT ACC   142
Cys Met Val Val Val Val Ala Thr Ile Lys Ser Val Ser Phe Tyr Thr
        35                  40                  45

CGG AAG GAT GGG CAG CTA ATC TAT ACC CCA TTC ACA GAA GAT ACC GAG   190
Arg Lys Asp Gly Gln Leu Ile Tyr Thr Pro Phe Thr Glu Asp Thr Glu
    50                  55                  60

ACT GTG GGC CAG AGA GCC CTG CAC TCA ATT CTG AAT GCT GCC ATC ATG   238
Thr Val Gly Gln Arg Ala Leu His Ser Ile Leu Asn Ala Ala Ile Met
65                  70                  75

ATC AGT GTC ATT GTT GTC ATG ACT ATC CTC CTG GTG GTT CTG TAT AAA   286
Ile Ser Val Ile Val Val Met Thr Ile Leu Leu Val Val Leu Tyr Lys
        80                  85                  90                  95

TAC AGG TGC TAT AAG GTC ATC CAT GCC TGG CTT ATT ATA TCA TCT CTA   334
Tyr Arg Cys Tyr Lys Val Ile His Ala Trp Leu Ile Ile Ser Ser Leu
            100                 105                 110

TTG TTG CTG TTC TTT TTT TCA TTC ATT TAC TTG GGG GAA GTG TTT AAA   382
Leu Leu Leu Phe Phe Phe Ser Phe Ile Tyr Leu Gly Glu Val Phe Lys
        115                 120                 125

ACC TAT AAC GTT GCT GTG GAC TAC ATT ACT GTT GCA CTC CTG ATC TGG   430
Thr Tyr Asn Val Ala Val Asp Tyr Ile Thr Val Ala Leu Leu Ile Trp
    130                 135                 140

AAT TTT GGT GTG GTG GGA ATG ATT TCC ATT CAC TGG AAA GGT CCA CTT   478
Asn Phe Gly Val Val Gly Met Ile Ser Ile His Trp Lys Gly Pro Leu
145                 150                 155

CGA CTC CAG CAG GCA TAT CTC ATT ATG ATT AGT GCC CTC ATG GCC CTG   526
Arg Leu Gln Gln Ala Tyr Leu Ile Met Ile Ser Ala Leu Met Ala Leu
160                 165                 170                 175

GTG TTT ATC AAG TAC CTC CCT GAA TGG ACT GCG TGG CTC ATC TTG GCT   574
Val Phe Ile Lys Tyr Leu Pro Glu Trp Thr Ala Trp Leu Ile Leu Ala
            180                 185                 190

GTG ATT TCA GTA TAT GAT TTA GTG GCT GTT TTG TGT CCG AAA GGT CCA   622
Val Ile Ser Val Tyr Asp Leu Val Ala Val Leu Cys Pro Lys Gly Pro
        195                 200                 205
```

-continued

```
                  195                 200                 205
CTT CGT ATG CTG GTT GAA ACA GCT CAG GAG AGA AAT GAA ACG CTT TTT        670
Leu Arg Met Leu Val Glu Thr Ala Gln Glu Arg Asn Glu Thr Leu Phe
        210                 215                 220

CCA GCT CTC ATT TAC TCC TCA ACA ATG GTG TGG TTG GTG AAT ATG GCA        718
Pro Ala Leu Ile Tyr Ser Ser Thr Met Val Trp Leu Val Asn Met Ala
    225                 230                 235

GAA GGA GAC CCG GAA GCT CAA AGG AGA GTA TCC AAA AAT TCC AAG TAT        766
Glu Gly Asp Pro Glu Ala Gln Arg Arg Val Ser Lys Asn Ser Lys Tyr
240                 245                 250                 255

AAT GCA GAA AGC ACA GAA AGG GAG TCA CAA GAC ACT GTT GCA GAG AAT        814
Asn Ala Glu Ser Thr Glu Arg Glu Ser Gln Asp Thr Val Ala Glu Asn
                260                 265                 270

GAT GAT GGC GGG TTC AGT GAG GAA TGG GAA GCC CAG AGG GAC AGT CAT        862
Asp Asp Gly Gly Phe Ser Glu Glu Trp Glu Ala Gln Arg Asp Ser His
            275                 280                 285

CTA GGG CCT CAT CGC TCT ACA CCT GAG TCA CGA GCT GCT GTC CAG GAA        910
Leu Gly Pro His Arg Ser Thr Pro Glu Ser Arg Ala Ala Val Gln Glu
        290                 295                 300

CTT TCC AGC AGT ATC CTC GCT GGT GAA GAC CCA GAG GAA AGG GGA GTA        958
Leu Ser Ser Ser Ile Leu Ala Gly Glu Asp Pro Glu Glu Arg Gly Val
    305                 310                 315

AAA CTT GGA TTG GGA GAT TTC ATT TTC TAC AGT GTT CTG GTT GGT AAA       1006
Lys Leu Gly Leu Gly Asp Phe Ile Phe Tyr Ser Val Leu Val Gly Lys
320                 325                 330                 335

GCC TCA GCA ACA GCC AGT GGA GAC TGG AAC ACA ACC ATA GCC TGT TTC       1054
Ala Ser Ala Thr Ala Ser Gly Asp Trp Asn Thr Thr Ile Ala Cys Phe
                340                 345                 350

GTA GCC ATA TTA ATT GGT TTG TGC CTT ACA TTA TTA CTC CTT GCC ATT       1102
Val Ala Ile Leu Ile Gly Leu Cys Leu Thr Leu Leu Leu Leu Ala Ile
            355                 360                 365

TTC AAG AAA GCA TTG CCA GCT CTT CCA ATC TCC ATC ACC TTT GGG CTT       1150
Phe Lys Lys Ala Leu Pro Ala Leu Pro Ile Ser Ile Thr Phe Gly Leu
        370                 375                 380

GTT TTC TAC TTT GCC ACA GAT TAT CTT GTA CAG CCT TTT ATG GAC CAA       1198
Val Phe Tyr Phe Ala Thr Asp Tyr Leu Val Gln Pro Phe Met Asp Gln
    385                 390                 395

TTA GCA TTC CAT CAA TTT TAT ATC TAGCATATTT GCGGTTAGAA TCCCATGGAT      1252
Leu Ala Phe His Gln Phe Tyr Ile
400                 405

GTTTCTTCTT TGACTATAAC CAAATCTGGG GAGGACAAAG GTGATTTTCC TGTGTCCACA     1312

TCTAACAAAG TCAAGATTCC CGGCTGGACT TTTGCAGCTT CCTTCCAAGT CTTCCTGACC     1372

ACCTTGCACT ATTGGACTTT GGAAGGAGGT GCCTATAGAA AACGATTTTG AACATACTTC     1432

ATCGCAGTGG ACTGTGTCCC TCGGTGCAGA AACTACCAGA TTTGAGGGAC GAGGTC        1488
```

(2) INFORMATION FOR SEQ ID NO:4:

(i) SEQUENCE CHARACTERISTICS:
        (A) LENGTH: 407 amino acids
        (B) TYPE: amino acid
        (D) TOPOLOGY: linear (ii) MOLECULE TYPE: protein (xi) SEQUENCE DESCRIPTION: SEQ ID NO:4:

```
Gln Val Val Glu Gln Asp Glu Glu Asp Glu Glu Leu Thr Leu Lys
 1               5                  10                  15

Tyr Gly Ala Lys His Val Ile Met Leu Phe Val Pro Val Thr Leu Cys
            20                  25                  30
```

Met Val Val Val Ala Thr Ile Lys Ser Val Ser Phe Tyr Thr Arg
            35                  40                  45

Lys Asp Gly Gln Leu Ile Tyr Thr Pro Phe Thr Glu Asp Thr Glu Thr
 50                  55                  60

Val Gly Gln Arg Ala Leu His Ser Ile Leu Asn Ala Ala Ile Met Ile
 65                  70                  75                  80

Ser Val Ile Val Val Met Thr Ile Leu Leu Val Val Leu Tyr Lys Tyr
                    85                  90                  95

Arg Cys Tyr Lys Val Ile His Ala Trp Leu Ile Ile Ser Ser Leu Leu
                100                 105                 110

Leu Leu Phe Phe Phe Ser Phe Ile Tyr Leu Gly Glu Val Phe Lys Thr
            115                 120                 125

Tyr Asn Val Ala Val Asp Tyr Ile Thr Val Ala Leu Leu Ile Trp Asn
130                 135                 140

Phe Gly Val Val Gly Met Ile Ser Ile His Trp Lys Gly Pro Leu Arg
145                 150                 155                 160

Leu Gln Gln Ala Tyr Leu Ile Met Ile Ser Ala Leu Met Ala Leu Val
                165                 170                 175

Phe Ile Lys Tyr Leu Pro Glu Trp Thr Ala Trp Leu Ile Leu Ala Val
                180                 185                 190

Ile Ser Val Tyr Asp Leu Val Ala Val Leu Cys Pro Lys Gly Pro Leu
            195                 200                 205

Arg Met Leu Val Glu Thr Ala Gln Glu Arg Asn Glu Thr Leu Phe Pro
210                 215                 220

Ala Leu Ile Tyr Ser Ser Thr Met Val Trp Leu Val Asn Met Ala Glu
225                 230                 235                 240

Gly Asp Pro Glu Ala Gln Arg Arg Val Ser Lys Asn Ser Lys Tyr Asn
                245                 250                 255

Ala Glu Ser Thr Glu Arg Glu Ser Gln Asp Thr Val Ala Glu Asn Asp
                260                 265                 270

Asp Gly Gly Phe Ser Glu Glu Trp Glu Ala Gln Arg Asp Ser His Leu
            275                 280                 285

Gly Pro His Arg Ser Thr Pro Glu Ser Arg Ala Ala Val Gln Glu Leu
            290                 295                 300

Ser Ser Ser Ile Leu Ala Gly Glu Asp Pro Glu Glu Arg Gly Val Lys
305                 310                 315                 320

Leu Gly Leu Gly Asp Phe Ile Phe Tyr Ser Val Leu Val Gly Lys Ala
                325                 330                 335

Ser Ala Thr Ala Ser Gly Asp Trp Asn Thr Thr Ile Ala Cys Phe Val
            340                 345                 350

Ala Ile Leu Ile Gly Leu Cys Leu Thr Leu Leu Leu Leu Ala Ile Phe
            355                 360                 365

Lys Lys Ala Leu Pro Ala Leu Pro Ile Ser Ile Thr Phe Gly Leu Val
370                 375                 380

Phe Tyr Phe Ala Thr Asp Tyr Leu Val Gln Pro Phe Met Asp Gln Leu
385                 390                 395                 400

Ala Phe His Gln Phe Tyr Ile
                405

(2) INFORMATION FOR SEQ ID NO:5:

(i) SEQUENCE CHARACTERISTICS:
        (A) LENGTH: 110 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

CTATACGAAG NGCAGAGAAA TAAGGCCTAC TTCACAAGCG CCTTCCCCCG TAATGATATC      60

ATCTCAACTT AGTATTATAC CCACACCCAC CCAAGAATAG GGTTTAAAAA                110

(2) INFORMATION FOR SEQ ID NO:6:

(i) SEQUENCE CHARACTERISTICS:
            (A) LENGTH: 210 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:6:

CTCTATTGGT CTGAACTGTT CTTTCACGTT TCCCATTTCC CTGTGGCTCA CTGTGCTTAC      60

AATCACTGCT GTGGAATCAT GATACCACTT TTAGCTCTTT GTATCTTCCT TCAGTGTATT     120

TTTGTTTTTC AAGAGTAAGT AGATTTTAAC TGGACAACTT TGAGTACTGA CATCATTGAT     180

AAATAAACTG GCTTGTGGTT TCAATAAAAA                                     210

(2) INFORMATION FOR SEQ ID NO:7:

(i) SEQUENCE CHARACTERISTICS:
            (A) LENGTH: 373 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:7:

CACACCCGAG CAAAACTGTT TATTCTTGAG AAGTTCCATC TTCATTTCTG CCACAGTTGG      60

AACTTCCCGA GGAAGGAAGG AGGCCTGAGG TTTTGCACAA TCTGTTTCAG AGCCTGTTTA     120

GACTCAAACC TATGCTTCCC TTGGCAGCAG AATACACTTA ACCTAAAGCA GTATTTGGAG     180

TTGAGAAAAA CCTGGTGGGG TAAGTGAATA TGTACTGTTT GGTAGGGTAG GTAGAGAAGC     240

TGTGCTTTGA CCCTGTGATT CCATCTTTTT CTACCTTCTA TGATGGTGAT GAAGCTAGAT     300

ACCCCTAGGG AAGAAAGAAG GACTGGGTTT AGCAAAAATG ATTTGGTAAA TAAAGTTTAT     360

TTGAACACAA AAA                                                       373

(2) INFORMATION FOR SEQ ID NO:8:

(i) SEQUENCE CHARACTERISTICS:
            (A) LENGTH: 378 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:8:

CTGAGGACCT TTTGTCTGAG AATCAGTAGT GTTTTAAGGT GCTGATATCG AATTAATGAA      60

GTAAAGTTGT TGATGGTGGT GAAACACCGT AGGGCATGTG GTTCAAAGAG AAGCAGGAGG     120

GCAAGGGAAA GTTACCCTGA TCTTAGTTTG TAGCTTATGA CTTATTTAAT GAATGGATGC     180

CCAGCCAAGC TCAGAGTAGG CGCCCAAAGC ATTGTGGAGT AGTTTCCTGT TTTGTCTTTT     240

TTTTTTTTTT TTTTTAAGCC ATGACATCCC AGAAGAGGAC AGTGAATTAC TCCTAGGTCG     300

```
GCTCTTATAG AGTGGCCATA GTGTTCTGTC AAAACACTTG CTTCCATTTT CAGAGATAAA      360

AATCATTGAT TACAAAAA                                                   378

(2) INFORMATION FOR SEQ ID NO:9:

(i) SEQUENCE CHARACTERISTICS:
        (A) LENGTH: 270 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

TCAGGTGATG ACCGTCCGCT CCTAGTTCAC TGCTAGCTCA GCCTGAGGTT GCAGACTGGT       60

CTGAAGGTGT ACAGGTGCCC TCTGTGCCTA TTCAGCAATT CCCTACTGAA GACTGGAGCG      120

CTCAGCCTGC CACGAACTGG ACTGCAGCTC CACTGCTCAG GCCAACTGAA TGGGTAGGAG      180

CAACCACTGA CTGGTCTAAG CTGTTCTTGC ATAGGCTCTT AAGCAGCATG GAAAAATGGT     240

TGATGGAAGA TAAACATCAG TTTCTAAAAA                                      270

(2) INFORMATION FOR SEQ ID NO:10:

(i) SEQUENCE CHARACTERISTICS:
        (A) LENGTH: 160 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:

AGTTCTAAGG CTGCTGCTAA TTACANNNNN NNNNNNNNNN GCTGACCTAG AAGCAGCACC       60

ATTCCCATTT CCTCAGTACC CACAAAGTGC AGCCCACATT GGAGCCCCAG ACACCCTCT      120

GCAGCCATTG ACTGCAACTT GTTCTTTTGC CCATTAAAAA                           160

(2) INFORMATION FOR SEQ ID NO:11:

(i) SEQUENCE CHARACTERISTICS:
        (A) LENGTH: 270 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:11:

AAGAGAGTGA AACAGCCACC TGTGTCACTG TGCCCGTCCA TGCTGACCTG TGTTCCTCCC       60

CAGTCTCTTC TTGTTCCAGA GAGGTGGGGC TGATGTCTCC ATCTCTGTCT CACTTTATGT     120

GCACTGAGCT GCAACTTCTT ACTTCCCTAC TGAAAATAGA TCTGAATACG ATTGTTCTC      180

AATATTGCTA TGAGAGGTTG ATGATTAATT AAATAAGTCA ATTCCTGGAA GTGAGAGAGC     240

AAATAAAGAC CTGAGAACCT TCCAGAAAAA                                      270

(2) INFORMATION FOR SEQ ID NO:12:

(i) SEQUENCE CHARACTERISTICS:
        (A) LENGTH: 160 base pairs
        (B) TYPE: nucleic acid
        (C) STRANDEDNESS: double
        (D) TOPOLOGY: linear (ii) MOLECULE TYPE: DNA (genomic)
```

(xi) SEQUENCE DESCRIPTION: SEQ ID NO:12:

```
TCGCAGATAC AGCTGTCAGG CTGCCTCCTG CCTTTTCTTT TGTAAAGACA AGACCCTTGG      60

AGTTTTAATT CTGTTTTGTA CTTCCTGTGG GGCCTCCACT GCTTTTCTAT GGGAGACACT     120

CTTAATTTAA CAGATGTGTA TATTTTGAAA CTCTGAAAAA                           160
```

(2) INFORMATION FOR SEQ ID NO:13:

(i) SEQUENCE CHARACTERISTICS:
        (A) LENGTH: 250 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:13:

```
GTCAGTTCGA TCGGCTCTAG TAGCCTGAGC ACTCATGCAG TCGCATGGCT CTGTGTCTCT      60

CTGGTCTTGT ACTTGGTGCA ATAGCAACTT CCCTACCCGT GCATTCCATC TTTCATGTTG     120

TGTAAAGTTC TTCACTTTTT TCTCTGAGGG CTGGGGGTTG GGGGAGTCAG CATGATTATA     180

TTTTAATGTA GAAAATGTGA CATCTGGATA TAAAATGAAG ATAAATGTTA AATTAAATGG     240

ACCTTAAAAA                                                            250
```

(2) INFORMATION FOR SEQ ID NO:14:

(i) SEQUENCE CHARACTERISTICS:
        (A) LENGTH: 270 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:14:

```
AAGTGTATCT TACTGTGCCT GTCAGGTTAC AAACTAGTGC GTTGACGCAC AGTGTCCAAG      60

TTATTAGAGC CCTTGTTAGC CAGACCCAGG TGTCCTGGTC ACCGTTTCAC CATCATGCTT     120

TGATGTTCCC CTGTCTTTCC CTCTTCTGCT CTCAAGAGCA AAGGTTAATT AAGGTGCAAA     180

GATGAAGTCA CTGTAAACTA ATCTGTCATT GTTTTTGCCT TCCTTTTCTT TTTCAGTGCA     240

GAAATTAAAA GTAAGTATAA AGCACAAAAA                                      270
```

(2) INFORMATION FOR SEQ ID NO:15:

(i) SEQUENCE CHARACTERISTICS:
        (A) LENGTH: 200 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:15:

```
TTGCAAGAAG TCAGAACNGG ATGGCTGGGT CTCCCCCTAC CTCTTCCAGC TCCCACAATT      60

TTNCCATGAT GAGGTAGCTT CTCCCTGGGC TCTCCTTCTT GCCTACCCTG TCTCCTGGGA     120

TCAGAGGGTA GTACAGAAGC CCTGACTCAT GCCTTGAGTA CATACCATAC AGCAAATAAN     180

TGGTAGCAAA ACATTAAAAA                                                 200
```

(2) INFORMATION FOR SEQ ID NO:16:

(i) SEQUENCE CHARACTERISTICS:
        (A) LENGTH: 362 base pairs (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:16:

```
AAGGAAGTGA AATCAAAGAC AGGCAGCCCG GCACCAGGCC TGAAACCAGC CCTGGGCCTG    60

CCTGGCCTAA AGCTAGTAGT TAAAAATCAA CTTACGACTT AGAACCTGAT GTTATCCGTA    120

GATTCCAAGC ATTGTATAAA AAAATTGTGA AACTCCCTGT TGTGTTCTGT ACCAGTGCAT    180

GAAACCCCTG TCACATATCC CCTAGATTGC TCAATCAATC NCGACCCTTT CATGTGAAAT    240

CTTTAGTGTT GTGAGCCCTN AAAAGGGACA GAAATTGTGC ACTTGAGGAG CTCAGATTTT    300

AAGGCTGTAG CTTGCCGATG CTCCCAGCTG AATAAAGCCC TTCCTTCNAC AACTCTGAAA    360

AA                                                                  362
```

(2) INFORMATION FOR SEQ ID NO:17:

(i) SEQUENCE CHARACTERISTICS:
        (A) LENGTH: 344 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

```
ACCATGGATT CATGGTTTAT TTTATTCAGT GAGTTATAAT TCATTAATAT TGTTATTAAA    60

AATTTGTTTT TCTTTTAAGA AATGTTATAT TTTGACAACT TCAGACTTAC AGAAAGATTA    120

TAAGAGGTAG NNCAAATAAT TTTTGGATAT TATTCCCCAA ATGTTAACAT TTTACTGCAT    180

TTACTTTATC CTTTCTCCCC CTTCTCCTCC TGTCTTTCTA GATGAATATG AATATAGGTA    240

CTTAATACAG ATTTTTTTTC TAAACTGTTT GTAGGTTGCA GACACGATGC CTCTTTATTT    300

CTAAATAATG TGTATTTCCT AAATAAAAGG AATTACCTTA AAAA                    344
```

(2) INFORMATION FOR SEQ ID NO:18:

(i) SEQUENCE CHARACTERISTICS:
        (A) LENGTH: 210 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

```
GTGACTGTGT ACTCTGCTGC TGCCGCCCTG CCCCAGAGCT CTCCTTGGCT GCGTCTGGCC    60

GGCTCTCATG GTACTTCCTC TGTGAACTGT GTGTGAATCT GCTTTTCCTC TGCTTCGGAG    120

GAAATTGTAA ATCCTGTGTT TCATTACTTG AATGTAGTTA TCTATTGAAA ATATATATTA    180

TATACATAGA CATATATATA TATATAAAAA                                    210
```

(2) INFORMATION FOR SEQ ID NO:19:

(i) SEQUENCE CHARACTERISTICS:
        (A) LENGTH: 310 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:19:

```
ACTCGATCTC TCACTAGACT GGCTGAAGTC CTACGTTCAG TGAAGATAAC TAAGTCCTGC      60

TTTCTCAGTA CGCATTGCGG GTTTTACCAT TCATCCTGTC TAAGGTCCTG GGTTTGGTGT     120

GAGCTTGGCG GCTGGTGGGT GGGGTTTTCA AGTGGGTCAC GGCGCTCTCG GCAGCCGGGG     180

ATGCGTGTCC GCACTGACAG CCTGTGAGAG TGCTCGGCCT AACCTTAGAA CACATTGTAA     240

CTGAATACAG TGTTTTCAAT TTGTACAGAA TAGTTAGNAT ATTCTATTAA AGTGGTGAAA     300

CATTGAAAAA                                                            310
```

(2) INFORMATION FOR SEQ ID NO:20:

(i) SEQUENCE CHARACTERISTICS:
        (A) LENGTH: 338 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:20:

```
GGGGCACCCT CCCTGGCCAC ACGCCTGTTC CCAGCAAGTG CTGAAACTCA CTAGACCGTC      60

TGCCTGTTTC GAAATGGGGA AAGCCGTGCG TGCGCGTTAT TTATTTAAGT GCGCCTGTGT     120

GCGCGGGTGT GGGAGCACAC TTTGCAAAGC CACAGCGTTT CTGGTTTTGG GTGTACAGTC     180

TTGTGTGCCT GGCGAGAAGA ATATTTTCTA TTTTTTTAAG TCATTTCATG TTTCTGTCTG     240

GGGAAGGCAA GTTAGTTAAG TATCACTGAT GTGGGTTGAG ACCAGCACTC TGTGAAACCT     300

TGAAATGAGA AGTAAAGGCA GATGAAAAGA AAGAAAAA                             338
```

(2) INFORMATION FOR SEQ ID NO:21:

(i) SEQUENCE CHARACTERISTICS:
        (A) LENGTH: 170 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:21:

```
TCTACTCGAA ACGCAGTACA CACTTTATCA GCCAGAGCTA GTCAGTCTGT GCTCCTGGCT      60

ATAAGACCCA GCCTGAGATG GTCCCATCTG CAGGGCCCGC ACCAGTTGGA CAGATGCCTC     120

CCCACCACCA ATTGCCAAAG GTCCAATAAA ATGCCTCAAC CACGGAAAAA                170
```

(2) INFORMATION FOR SEQ ID NO:22:

(i) SEQUENCE CHARACTERISTICS:
        (A) LENGTH: 180 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:22:

```
CTGCCAGTTT CAGGCCTCGG TCCATAGAGA CACCACCACC ATGGCCAGTG AAAGGTATAG      60

TCCTGCAGCA GCTGTCTCCT GGTGCAGGTG CCTGCCAGCC CACTGGATTG GGACGGGCCA     120

GGCTGGGCCA GGTCGGGGGC TCAGTCTGGG AGGTAATAAA AGCAGACCGA CACGCAAAAA     180
```

(2) INFORMATION FOR SEQ ID NO:23:

(i) SEQUENCE CHARACTERISTICS:

(A) LENGTH: 110 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:23:

GGCAAGCAGN TTCTGGTGGG TGTGTGGTGG TACCTCACTG TGGTTTTGGT TTGCGTTTTC      60

CTCTATTTGC ACAAAATGAT ATTAAATATA TTTTATGCTT ATTAGTCATT                 110

(2) INFORMATION FOR SEQ ID NO:24:

(i) SEQUENCE CHARACTERISTICS:
        (A) LENGTH: 90 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:24:

CAGAAGGTCT GCCATGGAGT TGCAGTCATC ACGGTAGATG GCGTATGATT TTGCTGAATT      60

TTAAATAAAA TGAAAACCAT AAATTAAAAA                                        90

(2) INFORMATION FOR SEQ ID NO:25:

(i) SEQUENCE CHARACTERISTICS:
        (A) LENGTH: 433 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:25:

TAAAATTTCG GTTGGGCGAC CTCGGAGCAG AACCAACCTC CGAGCAGTAC ATGCTAAGAC      60

TTCACCAGTC AAAGCGAACT ACTATACTCA ATTGATCCAA TAACTTGACC AACGGAACAA     120

GTTACCCTAG GGATAACAGC GCAATCCTAT TCTAGAGTCC ATATCAACAA TAGGGTTTAC     180

GACCTCGATG TTGGATCAGG ACATCCCGAT GGTGCAGCCG CTATTAAAGG TTCGTTTGTT     240

CAACGATTAA AGTCCTACGT GATCTGAGTT CAGACCGGAG TAATCCAGGT CGGTTTCTAT     300

CTACTTCAAA TTCCTCCCTG TACGAAAGGA CAAGAGAAAT AAGGCCTACT TCACAAAGCG     360

CCTTCCCCGT AAATGATATC ATCTCAACTT AGTATTATAC CCACACCCAC CCAAGAACAG     420

GGTTTGTTAA AAA                                                         433

(2) INFORMATION FOR SEQ ID NO:26:

(i) SEQUENCE CHARACTERISTICS:
        (A) LENGTH: 366 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:26:

ATTACAATTC AGTTTCTGTG ACATCTTTTT AAACCACTGG AGGAAAAATG AGATATTCTC      60

TAATTTATTC TTCTATAACA CTCTATATAG AGCTATGTGA GTNCTAATCA CATTGAATAA     120

TAGTTATAAA ATTATTGTAT AGACATCTGC TTCTTAAACA GNTTGTGAGT TCTTTGAGAA     180

ACAGCGTGGA TTTTACTTAT CTGTGTATTC ACAGAGCTTA GCNCAGTGCC TGGTAATGAG     240

```
CAAGCATACT TGCCATTACT TTTCCTTCCC ACTCTCTCCA ACATCACATT CACTTTAAAT      300

TTTTCTGTAT ATAGAAAGGA AAACTAGCCT GGGCAACATG ATGAAACCCC ATCTCCACTG      360

CAAAAA                                                                366
```

(2) INFORMATION FOR SEQ ID NO:27:

(i) SEQUENCE CHARACTERISTICS:
        (A) LENGTH: 200 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:27:

```
TAAGTAGTAG AAGCTGTTAA TATACATGCA TCGTAACCTC AGAAGCAAGA GAATGTTTTG       60

TGGACCACTT TGGTTTTCTT TTTTGCGTGT GGCAGTTTTA AGTTATTAGT TTTTAAAATC      120

AGTACTTTTT AATGGAAACA ACTTGACCAA AAATTTGTCA CAGAATTTTG AGACCCATTA      180

AAAAAGTTAA ATGAGAAAAA                                                 200
```

(2) INFORMATION FOR SEQ ID NO:28:

(i) SEQUENCE CHARACTERISTICS:
        (A) LENGTH: 2276 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:28:

```
CTCTACCGGA TCCACTATTA CGGGGGGGGG GGGGGGGGCT GGACCGCGGC GGCAGAAACA       60

GGCATTTCCA GCAGTGAGGA GACAGCCAGA AGCAAGCTTT TGGAGCTGAA GGAACCTGAG      120

ACAGAAGCTA GTCCCCCCTC TGAATTTTAC TGATGAAGAA ACTGAGGCCA CAGAGCTAAA      180

GTGACTTTTC CAAGGTCGC  CCAGCGAGGA CGTGGGACTT CTCAGACGTC AGGAGAGTGA      240

TGTGAGGGAG CTGTGTGACC ATAGAAAGTG ACGTGTTAAA AACCAGCGCT GCCCTCTTTG      300

AAAGCCAGGG AGCATCATTC ACTTAGCCTG CTGAGAAGAA GAAACCAAGT GTCCGGGATT      360

CAGACCTCTC TGCGGCCCCA AGTGTTCGTG GTGCTTCCAG AGGCAGGGCT ATGCTCACAT      420

TCATGGCCTC TGACAGCGAG GAAGAAGTGT GTGATGAGCG GACGTCCCTA ATGTCGGCCG      480

AGAGCCCCAC GCCGCGCTCC TGCCAGGAGG GCAGGCAGGG CCCAGAGGAT GGAGAGAACA      540

CTGCCCAGTG GAGAAGCCAG GAGAACGAGG AGGACGGTGA GGAGGACCCT GACCGCTATG      600

TCTGTAGTGG GGTTCCCGGG CGGCCGCCAG GCCTGGAGGA AGAGCTGACC CTCAAATACG      660

GAGCGAAGCA CGTGATCATG CTGTTTGTGC CTGTCACTCT GTGCATGATC GTGGTGGTAG      720

CCACCATCAA GTCTGTGCGC TTCTACACAG AGAAGAATGG ACAGCTCATC TACACGCCAT      780

TCACTGAGGA CACACCCTCG GTGGGCCAGC GCCTCCTCAA CTCCGTGCTG AACACCCTCA      840

TCATGATCAG CGTCATCGTG GTTATGACCA TCTTCTTGGT GGTGCTCTAC AAGTACCGCT      900

GCTACAAGTT CATCCATGGC TGGTTGATCA TGTCTTCACT GATGCTGCTG TTCCTCTTCA      960

CCTATATCTA CCTTGGGGAA GTGCTCAAGA CCTACAATGT GGCCATGGAC TACCCCACCC     1020

TCTTGCTGAC TGTCTGGAAC TTCGGGGCAG TGGGCATGGT GTGCATCCAC TGGAAGGGCC     1080

CTCTGGTGCT GCAGCAGGCC TACCTCATCA TGATCAGTGC GCTCATGGCC CTAGTGTTCA     1140

TCAAGTACCT CCCAGAGTGG TCCGCGTGGG TCATCCTGGG CGCCATCTCT GTGTATGATC     1200
```

-continued

```
TCGTGGCTGT GCTGTGTCCC AAAGGGCCTC TGAGAATGCT GGTAGAAACT GCCCAGGAGA    1260

GAAATGAGCC CATATTCCCT GCCCTGATAT ACTCATCTGC CATGGTGTGG ACGGTTGGCA    1320

TGGCGAAGCT GGACCCCTCC TCTCAGGGTG CCCTCCAGCT CCCCTACGAC CCGGAGATGG    1380

AAGACTCCTA TGACAGTTTT GGGGAGCCTT CATACCCCGA AGTCTTTGAG CCTCCTTGA     1440

CTGGCTACCC AGGGGAGGAG CTGGAGGAAG AGGAGGAAAG GGGCGTGAAG CTTGGCCTCG    1500

GGGACTTCAT CTTCTACAGT GTGCTGGTGG GCAAGGCGGC TGCCACGGGC AGCGGGGACT    1560

GGAATACCAC GCTGGCCTGC TTCGTGGCCA TCCTCATTGG CTTGTGTCTG ACCCTCCTGC    1620

TGCTTGCTGT GTTCAAGAAG GCGCTGCCCG CCCTCCCCAT CTCCATCACG TTCGGGCTCA    1680

TCTTTTACTT CTCCACGGAC AACCTGGTGC GGCCGTTCAT GGACACCCTG GCCTCCCATC    1740

AGCTCTACAT CTGAGGGACA TGGTGTGCCA CAGGCTGCAA GCTGCAGGGA ATTTTCATTG    1800

GATGCAGTTG TATAGTTTTA CACTCTAGTG CCATATATTT TTAAGACTTT TCTTTCCTTA    1860

AAAAATAAAG TACGTGTTTA CTTGGTGAGG AGGAGGCAGA ACCAGCTCTT TGGTGCCAGC    1920

TGTTTCATCA CCAGACTTTG GCTCCCGCTT TGGGGAGCGC CTCGCTTCAC GGACAGGAAG    1980

CACAGCAGGT TTATCCAGAT GAACTGAGAA GGTCAGATTA GGGCGGGGAG AAGAGCATCC    2040

GGCATGAGGG CTGAGATGCG CAAAGAGTGT GCTCGGGAGT GGCCCCTGGC ACCTGGGTGC    2100

TCTGGCTGGA GAGGAAAAGC CAGTTCCCTA CGAGGAGTGT TCCCAATGCT TTGTCCATGA    2160

TGTCCTTGTT ATTTTATTGC CTTTAGAAAC TGAGTCCTGT TCTTGTTACG GCAGTCACAC    2220

TGCTGGGAAG TGGCTTAATA GTAATATCAA TAAATAGATG AGTCCTGTTA GAAAAA        2276
```

(2) INFORMATION FOR SEQ ID NO:29:

(i) SEQUENCE CHARACTERISTICS:
  (A) LENGTH: 447 amino acids
  (B) TYPE: amino acid
  (C) STRANDEDNESS:
  (D) TOPOLOGY: linear (ii) MOLECULE TYPE: protein (xi) SEQUENCE DESCRIPTION: SEQ ID NO:29:

```
Met Leu Thr Phe Met Ala Ser Asp Ser Glu Glu Val Cys Asp Glu
1               5                   10                  15

Arg Thr Ser Leu Met Ser Ala Glu Ser Pro Thr Pro Arg Ser Cys Gln
            20                  25                  30

Glu Gly Arg Gln Gly Pro Glu Asp Gly Glu Asn Thr Ala Gln Trp Arg
        35                  40                  45

Ser Gln Glu Asn Glu Glu Asp Gly Glu Glu Asp Pro Asp Arg Tyr Val
    50                  55                  60

Cys Ser Gly Val Pro Gly Arg Pro Pro Gly Leu Glu Glu Glu Leu Thr
65              70                  75                  80

Leu Lys Tyr Gly Ala Lys His Val Ile Met Leu Phe Val Pro Val Thr
                85                  90                  95

Leu Cys Met Ile Val Val Val Ala Thr Ile Lys Ser Val Arg Phe Tyr
            100                 105                 110

Thr Glu Lys Asn Gly Gln Leu Ile Tyr Thr Pro Phe Thr Glu Asp Thr
        115                 120                 125

Pro Ser Val Gly Gln Arg Leu Leu Asn Ser Val Leu Asn Thr Leu Ile
    130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
```

-continued

```
                        165                 170                 175
Leu Met Leu Leu Phe Leu Phe Thr Tyr Ile Tyr Leu Gly Glu Val Leu
            180                 185                 190

Lys Thr Tyr Asn Val Ala Met Asp Tyr Pro Thr Leu Leu Leu Thr Val
        195                 200                 205

Trp Asn Phe Gly Ala Val Gly Met Val Cys Ile His Trp Lys Gly Pro
    210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
            245                 250                 255

Gly Ala Ile Ser Val Tyr Asp Leu Val Ala Val Leu Cys Pro Lys Gly
            260                 265                 270

Pro Leu Arg Met Leu Val Glu Thr Ala Gln Glu Arg Asn Glu Pro Ile
        275                 280                 285

Phe Pro Ala Leu Ile Tyr Ser Ser Ala Met Val Trp Thr Val Gly Met
    290                 295                 300

Ala Lys Leu Asp Pro Ser Ser Gln Gly Ala Leu Gln Leu Pro Tyr Asp
305                 310                 315                 320

Pro Glu Met Glu Asp Ser Tyr Asp Ser Phe Gly Glu Pro Ser Tyr Pro
            325                 330                 335

Glu Val Phe Glu Pro Pro Leu Thr Gly Tyr Pro Gly Glu Glu Leu Glu
            340                 345                 350

Glu Glu Glu Arg Gly Val Lys Leu Gly Leu Gly Asp Phe Ile Phe
            355                 360                 365

Tyr Ser Val Leu Val Gly Lys Ala Ala Thr Gly Ser Gly Asp Trp
    370                 375                 380

Asn Thr Thr Leu Ala Cys Phe Val Ala Ile Leu Ile Gly Leu Cys Leu
385                 390                 395                 400

Thr Leu Leu Leu Leu Ala Val Phe Lys Lys Ala Leu Pro Ala Leu Pro
            405                 410                 415

Ile Ser Ile Thr Phe Gly Leu Ile Phe Tyr Phe Ser Thr Asp Asn Leu
            420                 425                 430

Val Arg Pro Phe Met Asp Thr Leu Ala Ser His Gln Leu Tyr Ile
            435                 440                 445
```

ASSAY FOR IDENTIFYING AGENTS THAT INHIBIT CHROMOSOME NON-DISJUNCTION

RELATED APPLICATION

This application is a 371 of PCT/US96/133 14, filed Aug. 15, 1996, which claims the benefit of U.S. Provisional Application No. 60/002,448, filed Aug. 16, 1995.

BACKGROUND OF THE INVENTION

It has been appreciated for some time that Alzheimer's Disease has a complex etiology. At least 15 percent of the cases appear to be due to the inheritance of an autosomal-dominant mutation, but the majority are "sporadic", showing no clear association with any identifiable genetic or environmental factor. Feldman, R. G., et al., Neurology, 13:811–824 1963; Heston, L. L., et al., *Arch Gen. Psychiat.*, 38:1084–1090 (1981); Terry, R. D., *Aging*, 7:11–14 (1978); Jarvik, L. F. and Matsuyama, S. S., "The Biological Substrates of Alzheimer's Disease", Academic Press, pp. 17–20 (1986). Even identical twins can show a large discordance in the age of onset of the disease. Nee, L. E., et al., *Neurology*, 37:359–363 (1987). Yet despite this variation, Alzheimer's Disease shows a uniform set of clinical and pathological features—progressive loss of memory and other intellectual functions beginning in middle to late life, coupled with neuronal cell loss in the higher centers of the brain. Price, D. L., *Ann. Rev. Neurosci.*, 9:489–512 (1986).

While much has been learned about the biochemistry and expression of the aberrant protein deposits that characterize Alzheimer's Disease, progress toward the development of methods for the diagnosis and treatment of the disease has been slow. This is due, at least in part, to the fact that the molecular basis for the disease pathology has remained obscure.

SUMMARY OF THE INVENTION

The present invention relates to a method of identifying genes which encode gene products (e.g. proteins and RNA) which cause chromosome missegregation, genes identified by the method, proteins encoded by the genes, antibodies which bind the gene product, a method of identifying agents which reduce (partially or totally) chromosome missegregation in cells, constructs useful in the method of identifying agents which reduce chromosome missegregation in cells, agents identified by the method, methods of preventing chromosome missegregation in cells and agents (including antibodies, peptides, antisense and complementary oligonucleotides and small organic molecules) useful in preventing chromosome missegregation. Also included are genes which hybridize to polynucleotides whose sequences are disclosed herein and which encode proteins which cause chromosome missegregation. As described herein, Applicant has shown that the incidence of trisomy 21 is higher in fibroblasts from individuals with Alzheimer's Disease than in fibroblasts from individuals without Alzheimer's Disease. Based in part on this result, Alzheimer's Disease arises from an accumulation of trisomy 21 cells during the life of the individual, resulting from chromosomal missegregation.

The present invention relates to an assay useful to identify genes whose expression causes chromosome missegregation. Twenty-two genes whose products promoted chromosome missegregation in the yeast assay were isolated from cells obtained from an individual with Alzheimer's Disease. These results provide evidence that genes which give rise to gene products which cause improper chromosome segregation play a role in causing Alzheimer's Disease by promoting the accumulation of trisomy 21 cells. Agents which reduce improper chromosome segregation will slow or inhibit the progression of Alzheimer's Disease.

One embodiment of the present invention is a method of detecting a gene which encodes a gene product which causes chromosome missegregation, thereby resulting in a disease condition. As a result of chromosome missegregation, total chromosome number in the progeny may be greater than, less than or the same as the number of chromosomes in cells in which missegregation does not occur. "Chromosome missegregation" includes processes which result in aneuploid cells, which include cells with an abnormal number of chromosomes. Aneuploid cells include hyperploid cells, which are cells with a greater than normal number of chromosomes, or hypoploid cells, which are cells with a lower than normal number of chromosomes. "Chromosome missegregation" also includes processes which result in chromosomes having one or more breaks or one or more translocations. A chromosome with a translocation is a chromosome which has been broken and recombined with a fragment from a different chromosome.

The method comprises providing cells, referred to as tester cells. Also provided is a plasmid suitable for growth and reproduction in the tester cells. The plasmid comprises 1) a gene obtained from an organism other than yeast, preferably a mammalian gene, referred to as a test gene, whose gene product is suspected of causing chromosome missegregation; and 2) control elements suitable for expressing or overexpressing the test gene in the tester cells. The plasmid is introduced or transfected into the tester cells, which are then exposed to conditions suitable for the tester cells to reproduce, thereby producing progeny cells. The number of aneuploid progeny cells, the number of progeny cells with a chromosome having a break(s) or the number of progeny cells with a chromosome having a translocation is assessed, directly or indirectly, and compared to a suitable control, e.g. progeny cells obtained from the tester cells transfected with a plasmid without the tester gene or having a non-functional tester gene. A greater number of aneuploid progeny cells or a greater number of progeny cells with a chromosome having a break or translocation compared with the control number is indicative that the test gene causes chromosome missegregation.

In a preferred embodiment, the tester cells are yeast cells having one or more chromosomes (preferably one) with a mutated centromere and a marker gene. The mutation in the centromere makes the chromosome(s) prone to improper segregation. The marker gene encodes a detectable/identifiable marker gene product, which gives a quantifiable indication of the number of the mutated chromosome(s) present in the tester cell. The number of aneuploid progeny cells is determined by quantifying the indication given by the marker gene product.

Another embodiment of the present invention is a method of screening for an agent which inhibits improper chromosome segregation. Such an agent is useful in treating a disease caused by a gene product which causes improper chromosome segregation. The method comprises providing tester cells, as described above, transformed with a plasmid suitable for growth and reproduction in the tester cells and comprising 1) a gene which encodes a gene product which causes a disease process as a consequence of improper chromosome segregation resulting in aneuploid cells or cells with one or more chromsomes having a break or a translocation and 2) the appropriate control elements for expressing or over-expressing the gene in the tester cells. The tester cells are exposed to an agent being tested for its ability to inhibit the disease process and to conditions suitable for the tester cells to grow and reproduce, thereby producing progeny cells. The number of aneuploid progeny cells or the number of progeny cells with a chromosome having a break or a translocation is then assessed, either directly or indirectly. A lesser number of aneuploid progeny cells or a lesser number of progeny cells with a chromosome having a break or translocation in the presence of the agent being tested than in the absence of the agent being tested is indicative that the agent inhibits chromosome missegregation.

The present invention can be used to screen for genes which cause Alzheimer's Disease, cancer and aging by promoting improper chromosome segregation. The present invention can also be used to screen for agents which inhibit chromosome missegregation and inhibit disease processes caused by genes encoding gene products which promote chromosome missegregation.

BRIEF DESCRIPTION OF THE FIGURES

FIG. 1 shows the polynucleotide sequence (SEQ ID NO: 1) of AD3/AD3LP (top line), the amino acid sequence of AD4/AD3L (second line) (SEQ ID NO: 2), the partial polynucleotide sequence of AD3 (bottom line) (SEQ ID NO: 3), the partial amino acid sequence from one reading frame of AD3 (third line) (SEQ ID NO: 4) and the sites of mutation in AD3 (indicated by bold letters immediately below the bottom line). Also shown are the cdc2 kinase motifs of the AD3 and AD4/AD3LP proteins, indicated by boxes.

FIG. 4 shows the polydeoxynucleotide sequence of an expressed sequence tag of human mitochondrial tRNA gene (SEQ ID NO: 5) from an individual with Alzheimer's Disease. The expressed gene containing the tag was shown to cause improper chromosome segregation in the yeast assay of the present invention.

FIG. 5 shows the polydeoxynucleotide sequence of an expressed sequence tag (SEQ ID NO: 6) from chromosome 11 of an individual with Alzheimer's Disease. The expressed gene containing the tag was shown to cause improper chromosome segregation in the yeast assay of the present invention.

FIG. 6 shows the polydeoxynucleotide sequence of an expressed sequence tag (SEQ ID NO: 7) from chromosome 12 of an individual with Alzheimer's Disease. The expressed gene containing the tag was shown to cause improper chromosome segregation in the yeast assay of the present invention.

FIG. 7 shows the polydeoxynucleotide sequence of an expressed sequence tag (SEQ ID NO: 8) from chromosome 12 of an individual with Alzheimer's Disease. The expressed gene containing the tag was shown to cause improper chromosome segregation in the yeast assay of the present invention.

FIG. 8 shows the polydeoxynucleotide sequence of an expressed sequence tag (SEQ ID NO: 9) from human laminin receptor on chromosome 3 of an individual with Alzheimer's Disease. The expressed gene containing the tag was shown to cause improper chromosome segregation in the yeast assay of the present invention.

FIG. 9 shows the polydeoxynucleotide sequence of an expressed sequence tag (SEQ ID NO: 10) from chromosome 17 of an individual with Alzheimer's Disease. The expressed gene containing the tag was shown to cause improper chromosome segregation in the yeast assay of the present invention.

FIG. 10 shows the polydeoxynucleotide sequence of an expressed sequence tag (SEQ ID NO: 11) from human HLABS1 surface antigen on chromosome 6 of an individual with Alzheimer's Disease. The expressed gene containing the tag was shown to cause improper chromosome segregation in the yeast assay of the present invention.

FIG. 11 shows the polydeoxynucleotide sequence of an expressed sequence tag (SEQ ID NO: 12) from an individual with Alzheimer's Disease. The expressed gene containing the tag was shown to cause improper chromosome segregation in the yeast assay of the present invention.

FIG. 12 shows the polydeoxynucleotide sequence of an expressed sequence tag (SEQ ID NO: 13) from human $H^+$ATPase subunit B on chromosome 18 of an individual with Alzheimer's Disease. The expressed gene containing the tag was shown to cause improper chromosome segregation in the yeast assay of the present invention.

FIG. 13 shows the polydeoxynucleotide sequence of an expressed sequence tag (SEQ ID NO: 14) from an individual with Alzheimer's Disease. The expressed gene containing the tag was shown to cause improper chromosome segregation in the yeast assay of the present invention.

FIG. 14 shows the polydeoxynucleotide sequence of an expressed sequence tag (SEQ ID NO: 15) from chromosome 17 of an individual with Alzheimer's Disease. The expressed gene containing the tag was shown to cause improper chromosome segregation in the yeast assay of the present invention.

FIG. 15 shows the polydeoxynucleotide sequence of an expressed sequence tag (SEQ ID NO: 16) from chromosome 17 of an individual with Alzheimer's Disease. The expressed gene containing the tag was shown to cause improper chromosome segregation in the yeast assay of the present invention.

FIG. 16 shows the polydeoxynucleotide sequence of an expressed sequence tag (SEQ ID NO: 17) from chromosome 10 of an individual with Alzheimer's Disease. The expressed gene containing the tag was shown to cause improper chromosome segregation in the yeast assay of the present invention.

FIG. 17 shows the polydeoxynucleotide sequence of an expressed sequence tag (SEQ ID NO: 18) from human protein kinase C, δ subunit on chromosome 5 of an individual with Alzheimer's Disease. The expressed gene containing the tag was shown to cause improper chromosome segregation in the yeast assay of the present invention.

FIG. 18 shows the polydeoxynucleotide sequence of an expressed sequence tag (SEQ ID NO: 19) from an individual with Alzheimer's Disease. The expressed gene containing the tag was shown to cause improper chromosome segregation in the yeast assay of the present invention.

FIG. 19 shows the polydeoxynucleotide sequence of an expressed sequence tag (SEQ ID NO: 20) from an individual with Alzheimer's Disease. The expressed gene containing the tag was shown to cause improper chromosome segregation in the yeast assay of the present invention.

FIG. 20 shows the polydeoxynucleotide sequence of an expressed sequence tag (SEQ ID NO: 21) from human histidine tRNA synthase gene on chromosome 9 from an individual with Alzheimer's Disease. The expressed gene containing the tag was shown to cause improper chromosome segregation in the yeast assay of the present invention.

FIG. 21 shows the polydeoxynucleotide sequence of an expressed sequence tag (SEQ ID NO: 22) on chromosome 9 from an individual with Alzheimer's Disease. The expressed gene containing the tag was shown to cause improper chromosome segregation in the yeast assay of the present invention.

FIG. 22 shows the polydeoxynucleotide sequence of an expressed sequence tag (SEQ ID NO: 23) on chromosome 15 from an individual with Alzheimer's Disease. The expressed gene containing the tag was shown to cause improper chromosome segregation in the yeast assay of the present invention.

FIG. 23 shows the polydeoxynucleotide sequence of an expressed sequence tag (SEQ ID NO: 24) from an individual with Alzheimer's Disease. The expressed gene containing the tag was shown to cause improper chromosome segregation in the yeast assay of the present invention.

FIG. 24 shows the polydeoxynucleotide sequence of an expressed sequence tag (SEQ ID NO: 25) from an individual with Alzheimer's Disease. The expressed gene containing the tag was shown to cause improper chromosome segregation in the yeast assay of the present invention.

FIG. 25 shows the polydeoxynucleotide sequence of an expressed sequence tag (SEQ ID NO: 26) from an individual with Alzheimer's Disease. The expressed gene containing the tag was shown to cause improper chromosome segregation in the yeast assay of the present invention.

FIG. 26 shows the polydeoxynucleotide sequence of an expressed sequence tag (SEQ ID NO: 27) for human elongation factor 1a, shown to cause improper chromosome segregation in the yeast assay of the present invention.

FIGS. 28A–B show the complete polydeoxynucleotide sequence for AD4/ADLP3 (SEQ ID NO: 28).

FIG. 29 shows the complete amino acid sequence for AD4/ADLP3 (SEQ ID NO: 29).

DETAILED DESCRIPTION OF THE INVENTION

Figure 2:
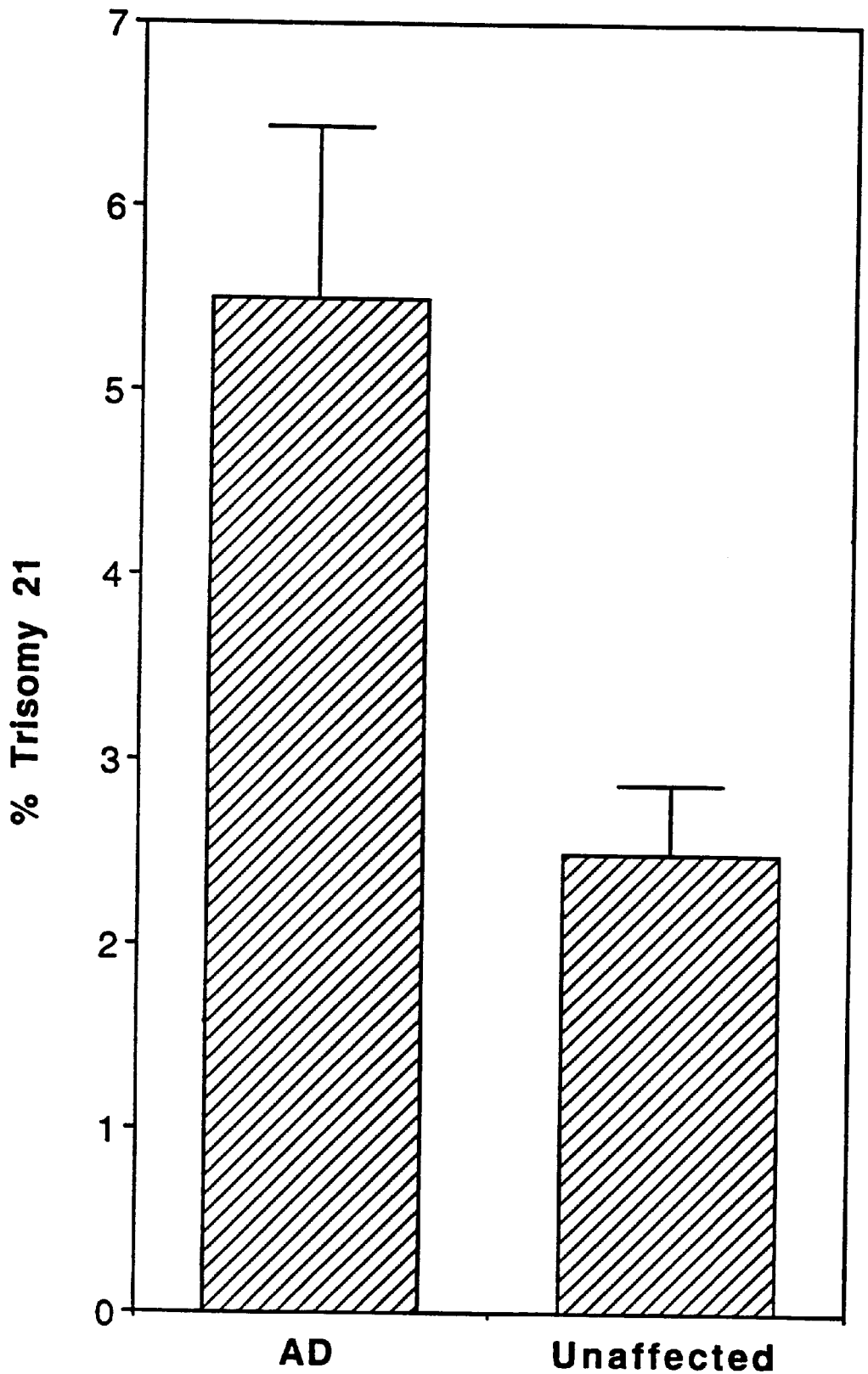
FIG. 2 is a graph showing the percentage of trisomy 21 cells in cultured fibroblasts from Alzheimer's Disease (AD) and unaffected individuals, as determined by fluorescence in situ hybridization. The greater frequency of trisomy 21 in the Alzheimer fibroblasts is significant at p=0.005.

Chromosome missegregation is associated with numerous human disorders. For example, individuals with Down syndrome have an extra chromosome 21, a condition which is referred to as trisomy 21. Alzheimer's Disease is a mosaic form of Down syndrome in which trisomy 21 cells accumulate over life time of the individual. As described herein, fibroblasts from individuals with Alzheimer's Disease show a statistically significant higher percentage of trisomy 21 than fibroblasts from individuals without the disease.

The fibroblasts were derived from individuals with chromosome 14-linked, chromosome 21-linked, early onset, or late onset disease. Increased trisomy 21 was found in all categories of individuals with Alzheimer's Disease examined (see Example 1).

Additional support for the trisomy 21 model of Alzheimer's Disease comes from the observation that individuals with Down syndrome and Alzheimer's Disease have many of the same symptoms. For example, Down syndrome individuals develop the neuropathology associated with Alzheimer's Disease by the fourth decade of life. In addition, Down syndrome individuals are hypersensitive to cholinergic antagonists such as atropine (Sacks and Smith, *J. Neurol. Neurosur. and Psych.* 52:1294 (1989) and Potter, *Am. J. Hum. Genet.* 48:1192 (1991). Specifically, when Down syndrome individuals are administered atropine or tropicamide in the eye, their pupils dilate at a lower concentration than is required to dilate the pupil of a normal individual. Alzheimer's individuals are highly sensitive to tropicamide and can be distinguished with 95% confidence from normal individuals or individuals with other neurodegenerative diseases (Scinto et al., *Science* 266:1051 (1994)).

This model of Alzheimer's Disease supports the conclusion that accumulation of cells with an extra chromosome 21 is caused by a mutated or overexpressed gene or genes which promote chromosome missegregation. "Chromosome non-disjunction," "chromosome missegregation" and "improper chromosome segregation" refer to processes which result in abnormal numbers of chromosomes in at least some members of a cell population. Such a cell is said to be "aneuploid." Cells with greater than normal numbers of chromosomes are "hyperploid", while cells with fewer than normal numbers of chromosomes are "hypoploid". "Chromosome non-disjunction," "chromosome missegregation" and "improper chromosome segregation" also refer to chromosomes with one or more breaks or which have been broken and then recombined with one or more fragments from another chromosome, i.e. the resulting chromosome comprises fragments from one or more fragmented chromosomes. Different genes may be involved in the chromosome missegregation that gives rise to different forms of Alzheimer's Disease, e.g. early onset versus late onset Alzheimer's Disease.

Chromosome missegregation is associated with numerous other human disorders besides Alzheimer's Disease and Down syndrome. Many cancer cells are hyperploid, sometimes at very early stages in the transformation process. Highly aneuploid tumor cells are especially prone to metastasis. Therefore, it is important to identify members of a potential new class of oncogene which, when overexpressed or mutant, causes chromosome missegregation and aneuploidy. Such genes are likely to be oncogenes. Hypoploid cells are also likely to be associated with cancerous tumors.

Elongation factor 1α (EF1α) has been identified as causing chromosome missegregation, using a yeast screen described below. A number of studies have shown the EF1α is overexpressed in many tumors and in cells able to divide in culture, but not in normal tissues of a living organism (Pencil and Nicolson, *Breast Cancer Research and Treatments* 25:165 (1993)). It has also been shown that overexpression of EF1α makes cells more prone to further transformation by chemical or physical carcinogens such as 3-methyl-cholanthrene or ultraviolet light (Shina et al. Science, 226:282 (1994) and Ghislain et al *Nature* 366:358 (1993)). Several observed functions of EF1α are consistent with EF1α causing chromosome missegregation. EF1α is an essential component of 26S protease complex, which is necessary for transition into anaphase. In addition, EF1α binds actin filaments and microtubules. It can also nucleate the polymerization of microtubules and has been reported to induce the severing of microtubules both in cell extracts and living cells when present at a high concentration. The latter activity is particularly likely to disrupt the microtubule apparatus of the spindle and lead to chromosome non-disjunction. Thus, it is likely that overexpression of certain genes, e.g. EF1α, or the expression of certain mutated genes cause aneuploidy and provide a necessary oncogenic event in the multistep process of carcinogenesis.

Normal aging also likely involves an increase in chromosome missegregation and the development of aneuploid cells. Therefore, genes identified as causing improper chromosome segregation as a result of mutation or overexpression may underlie the various symptoms of normal aging, in addition to Alzheimer's Disease and cancer.

The present invention is also based on the discovery that a cellular assay system can be used in a method of identifying mammalian genes which cause disease processes by promoting chromosome missegregation. A "disease process" includes a symptom or pathological consequence of a disease. Examples include memory loss and amyloid deposition in Alzheimer's Disease and tumor growth and metastasis in cancer. A gene which "promotes chromosome missegregation" results in significantly more chromosome missegregation when the gene is expressed than when it is not expressed. Such a gene can be a mutated gene which is expressed or wild type gene which is overexpressed. A gene which is "overexpressed" is expressed in amounts sufficiently greater than which normally occurs in the cell such that changes occur in the cell.

The method of the present invention comprises providing tester cells, for example yeast cells, mammalian cells such as human, rat, mouse cells and hamster cells and insect cells. Suitable mammalian cells include lymphoblasts and fibroblast cells.

In one embodiment the tester cells, preferably yeast cells, have a chromosome with a mutant centromere that makes the chromosome prone to improper chromosome segregation (a mutated chromosome) and a first marker gene on the mutated chromosome. A marker gene results in a marker gene product whose concentration is readily determined, either directly or indirectly (e.g. its concentration is proportional to the concentration of another gene product). The concentration of the marker gene product gives an indication of the number of mutant chromosomes; non-disjunctive events which give rise to hyperploidy of the chromosome with the mutated centromere result in increases in the number of marker genes, thereby resulting in increases in the concentration of the marker gene product. Non-disjunctive events which give rise to hypoploidy of the chromosome with the mutated centromere result in a decrease in the number of marker genes, thereby resulting in decreases in the concentration of the marker gene product. The concentration of the marker gene product is directly proportional to the number of chromosomes encoding the marker gene. The assay system can be pre-calibrated, e.g. the concentration of the marker gene product for one, two, three or more copies of the chromosome can be predetermined.

In one example, the first marker gene can give rise to a gene product which enhances or suppresses the expression of a second marker gene. The concentration of the gene product of the second marker gene is therefore proportional (directly or indirectly) to the concentration of the first marker gene product, and therefore proportional to the degree of aneuploidy, e.g. the number of extra chromosomes coding for the first marker gene. Preferably, the concentration of either marker can be assessed by a physical phenomenon which can be readily measured, e.g. color, enzyme assay or antibody detection (e.g. ELISA). The concentration of either marker gene thus indicates the degree of aneuploidy. In another example, the first marker gene product forms a complex with the second marker gene or marker gene product. In this case, the concentration of the complex is an indication of the degree of aneuploidy.

In the assay of the present invention, the tester cells are further modified to screen for mammalian genes which cause chromosome missegregation. Specifically, a mammalian gene, referred to as a test gene, suspected of encoding a product which causes chromosome missegregation, is introduced into the tester cells using an appropriate plasmid vector; the resulting tester cells, which contain the test gene, are maintained under conditions suitable for the gene to be expressed and reproduced by the tester cells. Suitable plasmid vectors typically contain an origin of replication (e.g. an autonomously replicating sequence when the plasmid is transformed into yeast), a yeast centromere and a growth origin suitable for growth and replication in the tester cells being transformed. The plasmid vector also contains a gene allowing for selection in the tester cells being transformed, e.g. a gene conferring resistance to an antibiotic provided in the growth medium (for example amp) or a gene allowing the tester cells to metabolize an essential nutrient supplied in the growth medium (for example trp). Typically, the plasmid also comprises genes suitable for selection and growth in an amplifying organism such as *E. Coli,* as discussed below. Optionally, the plasmid can contain one or more polycloning sites and/or a gene (e.g. lacz gene) which indicates incorporation of the transforming DNA into the plasmid. Suitable tester cells include yeast, mammalian cells (e.g. human and rodent cells), and insect cells. Plasmids are introduced into the tester cells by methods known in the art, for example electroporation, lithium chloride and by molecules that assist in the introduction of DNA into mammalian cells, such as Transfectam.

Suitable plasmids also have promoter sites which allow the gene being assessed to be expressed in the tester cells (e.g. SV40, gal 10 or other viral promoters). In some cases, it may be desirable to determine whether overexpression of the gene being assessed increases the rate of chromosome missegregation. In these cases, enhancer sites which increase the expression of the gene in the tester cells are also included in the plasmid. The degree of expression can also be increased or decreased by changing the sequence of the promoter site, according to methods known in the art.

In certain applications it may be advantageous to amplify the gene being screened before transforming the tester cells. In this case, the plasmid vector containing the gene is first introduced into an organism (referred to as an "amplifying organism") suitable for amplifying the plasmid. Suitable amplifying organisms include *E. coli,* gram negative organisms such as *Hemophilus influenzae* and *K. pneumoniae,* gram positive organisms such as *Bacillus subtilis* and eukaryotes such as yeast. The plasmid vector contains a gene suitable for selection in the amplifying organism. The amplifying organism is exposed to suitable growth conditions, thereby allowing the organism to reproduce and amplify the vector. The amplified plasmid vector can then be isolated from the culture and used to transform the tester cells.

After being transformed, the modified tester cells are exposed to conditions suitable for growth and reproduction, thereby producing progeny cells. Typically, a plasmid is used which allows selection of cells into which the plasmid has been incorporated, for example which confers resistance to an antibiotic. The cells are then generally allowed to grow for at least two to three cycles of reproduction before being selected. Cells grown for two to three cycles of reproduction can be analyzed for aneuploidy or chromosomes with breaks or translations, even though the plasmid has not been incorporated into the genome. Alternatively, the selected cells can be treated so that the plasmid is incorporated into the cellular genome, for example, by allowing the selected cells to grow for about 10–20 cycles of reproduction before being analyzed for aneuploid cells or cells with broken or translocated chromosomes.

The degree of aneuploidy in the progeny cells and the number of progeny cells having chromosomes with translocations can be determined by methods known in the art, for example by staining the cells and counting the number of abnormal cells. Methods for staining and determining the number of abnormal cells are disclosed, for example, in Sanchez et al., Lancet 1973:ii:269 (1973), the teachings of which are hereby incorporated herein by reference.

When the tester cells contain a marker gene the degree of aneuploidy is assessed by determining the concentration of one of the marker gene products. This concentration is compared with the concentration of the marker gene product in a suitable control, for example the concentration of the marker gene product in the progeny of tester cells that have been transformed with a plasmid that does not contain the gene being tested for its ability to cause chromosome missegregation. The control can be predetermined, or can be performed simultaneously with or subsequent to the assay which tests the mammalian gene for its ability to cause chromosome missegregation.

A concentration of one of the marker gene products in the progeny cells that differs from the concentration of one of the marker gene products in the control such that there is a greater degree of aneuploidy in the progeny cells than in the control cells indicates that the gene being tested causes chromosome missegregation. Typically, the concentration of one of the marker gene products is determined within subpopulations of progeny cells. A non-disjunction event in a cell will result in aneuploidy being passed on to the progeny of that cell alone. A non-disjunctive event can give rise to hypoploid progeny, hyperploid progeny or both. Consequently, the concentration of the marker gene product will be not be uniform throughout the colonies, but will differ from the control levels only in subpopulations, referred to as "sectors", which are progeny of a cell having undergone chromosome missegregation. Typically, the degree of aneuploidy is assessed by determining the number of sectors throughout the test colony, wherein a larger number of sectors is indicative of a higher degree of aneuploidy. The concentration of marker gene product within the sector and the overall concentration of the marker gene product throughout the test colonies are also indications of the ability of the gene to cause chromosome missegregation.

In a preferred embodiment more than one gene is introduced into the tester cells. It is more preferred that a cDNA library be used to transform the tester cells. The cDNA library is typically obtained from a cell or cells of an individual who has a disease which is believed to arise, at least in part, from a gene causing chromosome non-disjunction. Thus, this preferred embodiment is a method of identifying genes which are involved in disease processes resulting from improper chromosome segregation caused by the genes or their gene products. The cells are grown at low density to keep the progeny of individual clones from overlapping (e.g. about 200 original cells/100 mm plate with augar containing growth medium). Plasmids are recovered from sectors showing marker gene product concentrations which differ from control levels and sequenced. The resulting sequences are from genes which cause chromosome missegregation and are likely involved in the etiology of the disease.

In one example of a suitable assay system, a diploid yeast strain is constructed carrying an ochre mutation in the ade2 gene which determines the color of the yeast colonies grown on plates containing a limited (6 $\mu$g/ml) concentration of adenine. This yeast strain is described in Hieter, et al., Cell 40:381 (1985); McGrew, et al., Yeast, 5:271 (1989); Stoler, et al., Genes Dev., 9:573 (1995), the teachings of which are incorporated herein by reference. Cells homozygous for the ochre mutant ade2 gene (ade2-101) are red on these plates. The colonies are changed to pink or white by the presence of either one or two copies respectively of the sup11 gene. Sup11 encodes a suppressor tRNA molecule that can suppress the ochre mutation in the ade2-101 gene and allow production of the ade2 protein product, 5AIR carboxylase, an enzyme involved in purine biosynthesis. The sup11 gene in turn is placed on one specially altered yeast chromosome III that has a mutant centromere (cen130-3) that makes the chromosome prone (100-fold more than normal) to improper chromosome segregation. As a result, this yeast strain shows a high level of variable colored colonies and also colonies in which several colors occur at once to form "sectors." Sectored colonies indicate that during the growth of the colony from a single cell, the instability of the chromosome carrying the sup11 gene results in subclones containing zero, one, or two copies of that chromosome and thus cells which are either red, pink, or white respectively. As these cells divide, their progeny form the multi-colored sectors visible to the naked eye. Under normal conditions, the yeast strain so constructed shows a frequency of chromosome missegregation of about $10^{-5}$ as detected by the color assay (Stoler et al.). However, if a gene encoding a protein that increases chromosome missegregation is introduced into the tester strain, then the frequency of sectored colonies increases. One yeast gene involved in chromosome segregation have been identified in this manner (Stoler et al.).

The above assay was modified to screen for mammalian genes that cause chromosome missegregation, including mutant familial Alzheimer's Disease (FAD) genes. Specifically, a cDNA library was constructed from a human lymphoblastoid cell from a patient with chromosome 14linked FAD using a plasmid vector that can grow in either E. coli or yeast (pRS314.gal1-10). This plasmid contains the CEN6 yeast centromere, the ARSH4 yeast replication origin, a pBR322 origin for growth in E. coli, a trp gene for selection in yeast, an amp gene for selection in E. coli, and a poly-cloning site in the lacz gene. Library DNA was prepared and used to transform E. coli by electroporation (Potter, "Methods in Enzymology: Recombinant DNA Technology," Wu ed. Orlando, Fla., Academic Press, 1993). Cells that received a plasmid were selected by virtue of the ability of the plasmid to provide the trp gene (which is mutant in the yeast strain) and allow the cells to grow in the absence of tryptophan. Transformed cells were plated at relatively low density and the resulting colonies examined for multi-colored sectoring. Sectored colonies were recovered, desegregated into single cells and replated to confirm the cells' high sectoring phenotype. Plasmids were then recovered from the yeast clones showing high sectoring frequency and retransformed into the parent yeast strain to retest the specific cDNA's ability to induce increased chromosome segregation as revealed by sectored colonies.

Following several such sequential screening steps, twenty-two candidate genes were identified. Each gene caused increased levels of chromosome missegregation when expressed in the tester yeast strain and are therefore involved in one way or another in chromosome segregation. The increased chromosome missegregation may be due to overexpression in the target yeast cells of a normal gene involved in chromosome segregation, or to the presence of a mutation in a gene that yields an aberrant protein product that increases chromosome missegregation. Either of these two possibilities may cause the chromosome missegregation observed in the Alzheimer's cells from which the gene's cDNA was derived, and thus all of these twenty-two genes are potential candidates for being a causative agent in the development of Alzheimer's Disease. Partial sequences of these genes are given in FIGS. 4–25.

As described previously, missegregation of chromosomes is involved in the development of a number of different diseases. The assay described above identifies the genes which cause the improper chromosome segregation and, more specifically, genes which cause disease processes as a result of chromosome missegregation. Agents which prevent these genes from causing chromosome missegregation in the assay described above are likely to prevent chromosome missegregation in vivo and theerfore be useful in treating the disease caused by the aberrant gene.

Tester cells containing a chromosome with a mutated centromere, as described above, are particularly useful for identifying agents which inhibit chromosome missegregation. The effect of genes which cause chromosomal misseg-regation is amplified in these cells and therefore readily detectable. The chromosome with the mutated centromere is more prone to improper segregation than normal yeast chromosomes. When transformed into the tester cells as part of a suitable plasmid, genes which cause chromosomal missegregation cause a detectable change in the concentration of a marker gene product, indicative of a detectable increase in the rate of chromosome non-disjunction. This assay and therefore provides a convenient medium to test agents which inhibit chromosomal missegregation. Agents which decrease the rate of missegregation in tester cells transformed with a gene causing missegregation compared with untransformed tester cells are likely to slow the development of the disease caused by the gene and be useful in the treatment and/or development of treatments of the disease.

Another embodiment of the present invention is a method of identifying an agent which is an inhibitor of a disease process resulting from a gene which causes chromosome missegregation. The method comprises providing tester cells, as described above, additionally comprising a plasmid suitable for growth and reproduction in the tester cells. The plasmid also comprises a gene whose gene product results in the disease process by causing chromosome missegregation resulting in either aneuploid cells or cells with translocated chromosomes. The plasmid also comprises control elements allowing the gene to be expressed in the tester cells. In those cases where overexpression of the gene results in improper chromosome segregation, the plasmid also contains control elements, e.g., an enhancer site, which increases the level of expression of the gene in the tester cells. The tester cells are exposed to an agent being tested for its ability to inhibit the disease process and then to conditions suitable for the cell to grow and reproduce, thereby producing progeny cells. The number of aneuploid progeny cells and the number of progeny cells having translocated chromosomes are then assessed. A lesser number of aneuploid progeny cells or progeny cells having translocated chromosomes in the presence of the agent than in its absence is indicative that the agent inhibits chromosome missegregation and therefore also inhibits the disease process.

A suitable control is, for example, run by allowing tester cells which contain the gene which causes chromosome missegregation to grow and reproduce under the same conditions used in the test assay, but in the absence of the agent being assessed. The number of aneuploid progeny cells and the number of progeny cells with translocations are then assessed and compared to progeny cells grown in the presence of the agent, as described above. The control can be run prior to, simultaneously with or subsequent to the test assay.

There are numerous genes which can be used in the screening assay of the present invention to identify agents which can be used for the treatment of Alzheimer's Disease. For example, locus AD3, associated with susceptibility to early onset of Alzheimer's Disease has recently been mapped to a specific region on human chromosome 14. Five different mis-sense mutations (FIG. 1) have been found that cosegregate with early-onset familial Alzheimer's Disease (Sherrington et al., Nature 375:754 (1995)). It is predicted that these mutations result in increased levels of cells with trisomy 21 in carriers of the mutation compared with non-carriers. As a result, increased levels of chromosome mis-segregation will be observed when these mutated genes are used in an appropriate plasmid to transform the tester cells used in the assay of the present invention compared with untransformed tester cells. Agents which, when exposed to tester cells, decrease the degree of aneuploidy arising as a result of the expression of these mutated genes are likely to be agents useful in the treatment of Alzheimer's Disease.

Figure 27:
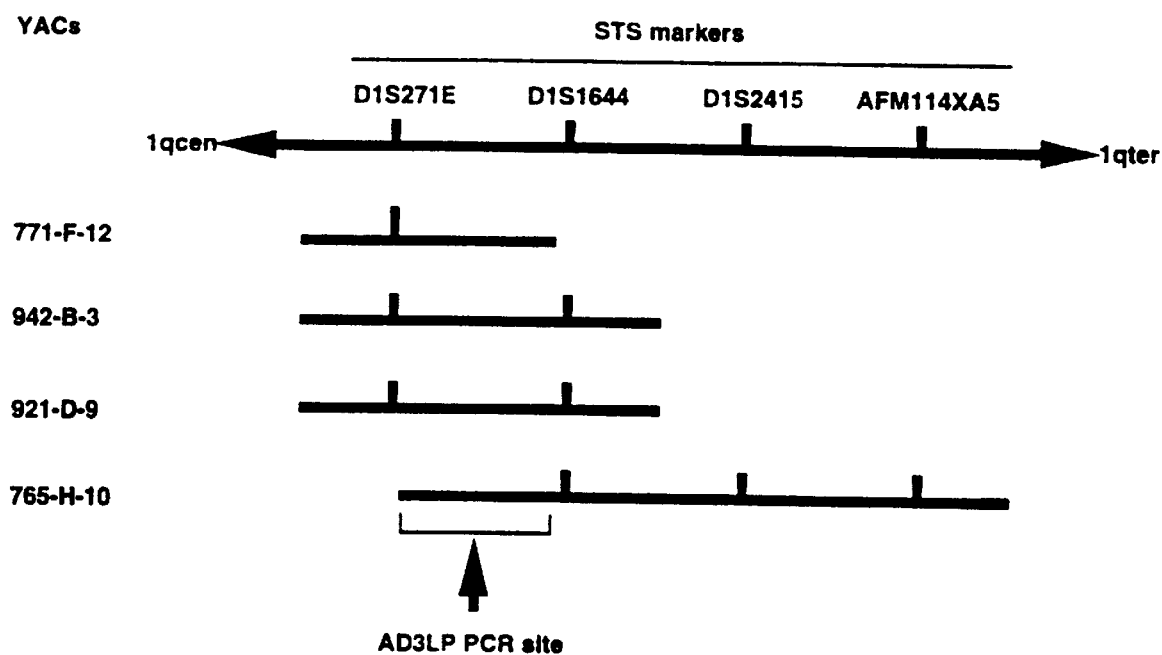
FIG. 27 is a map showing the localization of AD4/AD3LP on chromsome 1 and the yeast artifical chromsomes containing AD4/AD3LP used in the localization.

It is reported herein that the translation product of the gene (SEQ ID NO: 1 shows a portion of AD4/AD3LP) containing the expressed sequence tag of Accession No. T03796 (Genbank), referred to herein as "AD4/AD3LP" or "Presenilin 2", is highly homologous to AD3 (also referred to as "Presenilin 1") (Sherrington et al., 1995). Confirmation that AD4/AD3LP encodes a novel protein related to AD3 was obtained by genomic mapping. Oligonucleotide primers corresponding to AD4/AD3LP were used for PCR localization of the gene to chromosome 1 rather than chromosome 14, where AD3 resides. Sublocalization using YAC libraries have placed the gene corresponding to AD4/AD3LP to the long arm of chromosome 1, 289 centamorgans from the centromere (see FIG. 27). The complete polynucleotide sequence (SEQ ID NO: 28) and amino acid sequence (SEQ ID NO: 29) of AD4/AD3LP was determined, as described in Example 4.

AD4/AD3LP has four DNA binding motifs (S/T P X X). AP3 also has DNA binding domains. Thus, AD4/AD3LP and AD3 are likely involved in controlling gene expression or in the binding of chromatin to the nuclear membrane. Mutations in chromatin-binding proteins are known to cause chromosome missegregation. Therefore, the observation that AD4/AD3LP and AD3 have DNA binding motifs is consistent with AD4/AD3LP playing a role in causing familial and sporadic forms of Alzheimer's Disease The sites of mutation in AD3 leading to Alzheimer's Disease change amino acids that are identical between AD3 and AD4/AD3LP. For example, FIG. 1 shows the amino acid sequence of AD3, the amino acid sequence from one reading frame of AD4/AD3LP and the amino acid mutations leading to Alzheimer's Disease. It can be seen that the amino acids at these mutated positions in AD3 and the corresponding positions in AD4/AD3LP are identical. This observation coupled with the similarity of AD3 and AD4/AD3LP indicates a similarity of function and is consistent with AD4/AD3LP playing a role in causing familial and sporadic forms of Alzheimer's Disease as a result of mutations similar to those found in AD3. Consequently, AD4/AD3LP can also be used in the screening assay to identify new agents for the treatment of Alzheimer's Disease.

There are numerous genes which can be used in the screening assay of the present invention to identify agents which can be used for the treatment of cancer. For example, overexpression of EF1α, as described earlier, occurs in certain cancers and has been shown to result in highly aneuploid human cells in culture and increased susceptibility to transformation. Introduction of the EF1α gene into yeast and mammalian cells by a plasmid which results in its overexpression causes chromosome missegregation. Agents which reduce the level of chromosome missegregation in these transformed cells can be used in the treatment of cancer in which EF1α is overexpressed.

The twenty-two genes identified in the cellular assay as causing chromosome missegregation are likely to be involved in the development of cancer and Alzheimer's Disease. Consequently, these genes can also be used in the assay described above to screen for agents useful for the treatment of cancer and Alzheimer's Disease. The sequence for the entire gene can be routinely obtained by sequencing the entire plasmid isolated from clones in which non-disjunction is observed. Other genes thought to be involved in the development of Alzheimer's disease such as Apolipoprotein E, for examploe E2, E3 and E4, can also be used in the assay described above to screen for agents useful for the treatment of Alzheimer's Disease.

Another embodiment of the present invention is a polydeoxynucleotide having a sequence represented by SEQ ID NOS: 3, 6–8, 10, 12, 14–17, 19–20 and 22–26. These sequences represent novel polydeoxynucleotides (SEQ ID NOS: 6–8, 10, 12 and 25) or known polydeoxynucleotides with no known function SEQ ID NOS: 3, 14–17, 19–20, 22–24 and 26. Genes comprising these nucleic acids are useful in the assay described above in screening the agents for the treatment of Alzheimer's Disease and cancer and are included in the present invention.

These polydeoxynucelotides have many other uses. One example is as a gene marker, i.e. determining the presence or absence in a sample of the gene to which the a-polydeoxynucleotide hybridizes. The polydeoxynucleotide is labeled, e.g. with a radioactive group or a biotinylated group, and combined with the sample or restricted sample under hybridizing conditions and then amplified by polymerase chain reaction. The presence of the gene is indicated by the presence of labeled, amplified product. Identifying the presence or absence of a gene is particularly useful when the gene or a mutated form of the gene is known to cause a disease. In this instance, identifying the presence or absence of the gene in a sample which contains the genetic material of an individual can be used as a method of diagnosis for the disease. The presence of the form of AD4/AD3LP causing chromosomal missegregation, as described above, is likely to be useful in diagnosing Alzheimer's Disease, both before and after the onset of symptoms typically associated with the disease.

The polydeoxynucleotides of the present invention can also be used for chromosome walking and to assist in determining the nucleotide sequence in the vicinity of the gene, e.g. mapping a chromosome (Singer and Berg, Genes and Genomes, University Science Books, Mill Valley, Calif. (1991)). The chromosome or nucleic acids being mapped are divided into portions two of which are each digested with a different restriction enzyme. The polydeoxynucleotide is used as a probe to identify a fragment from each portion which hybridizes to the probe. The fragments are each sequenced and compared. New non-overlapping sequences can thereby be identified as sequences in the vicinity of the probe.

These polynucleotides are also useful in identifying polymorphic markers such as a sequence repeat. Polymorphic markers are identified by comparing the sequences from the genes of healthy individuals with those from individuals with a disease caused by a mutation in the gene being assessed. Genetic markers can also be identified by sequencing in the vicinity of the gene. Genetic markers can be used in genetic linkage studies, in the mapping of chromosomes and in determining the inheritance of human diseases, including cancer, developmental abnormalities and aging diseases.

Another embodiment of the present invention is a gene which is hybridizable to a polydeoxynucleotide represented by SEQ ID NO: 3, 6–8, 10, 12, 14–17, 19–20 and 22–26. These genes can be obtained by sequencing the entire plasmid from which the polydeoxynucleotide was obtained. These genes have the same uses described above for the polydeoxynucleotides described above. They can also be used for obtaining the genomic gene. A polydeoxydeoxynucleotide comprising the gene is used as a probe to isolate the fragments from a restriction enzyme digest to which it can hybridize. These fragments are then sequenced, thereby identifying regions in the genomic gene, e.g. introns, which do not appear in the cDNA gene.

The invention is further illustrated by the following examples, which are not intended to be limiting in any way.

EXEMPLIFICATION

EXAMPLE 1

Individuals with Alzheimer's Disease Have Higher Levels of Trisomy 21 in their Fibroblast Cells than Individuals Without Alzheimer's Disease Cell Lines—Human fibroblast cell lines were obtained primarily from the NIA Aging Cell Repository (Camden, NJ).

Cell lines containing a mutation in the amyloid precursor is protein were obtained from cells from affected family members by skin biopsy and then grown in culture.

Fluorescence in situ Hybridization (FISH)—Fibroblast cells growing directly on clean, uncoated glass slides were washed with PBS and fixed in cold MeOH: acetic acid, 3:1 for ten minutes. Fixed cells were permeabilized for 15 minutes in 0.5% Triton X-100 and 0.5% saponin in PBS, washed and stored until use in PBS containing 0.2% $NaN_3$. FISH was carried out according to a modification of the methods described by Lichter et al., Proc. Natl. Acad. Sci. USA, 85:9664 (1988). Slides were denatured in 70% formamide, 2× SSC (1× SSC is 0.15 M NaCl/0.015 M sodium citrate) pH 7.0 at 70° C. for 2 minutes then dehydrated in a cold ethanol series. Denatured probe prepared by nick translation (approximately 10 μg) was applied to the slides in a solution containing 50% formamide, 10% dextran sulphate, 2× SSC, and sheared DNA (herring sperm and Cot I) to block non-specific hybridization (commercially supplied probes were applied in a pre-made solution), coverslipped, and sealed with rubber cement. Hybridizations were carried out overnight at 37° C. in a humid chamber. Slides were then washed in either 50% formamide in 2× SSC, three times for two minutes each at 42° C. followed by three washes in 0.1× SSC at 60° C., or for two minutes in 2× SSC at 72° C.

Detection of Hybrids—Probes labeled with biotin or digoxigenin were detected using standard immunocytochemistry techniques. Hybridized and washed slides were rinsed in PN (0.1 M $NaPO_4$, 0.1% Nonidet P40), then incubated with FITC-conjugated avidin (Vector) or FITC-conjugated antidigoxigenin (Boehringer). After washing three times for two minutes each in PN, mounting medium containing propidium iodide (a red fluorescing DNA dye) or DAPI (a blue fluorescing DNA dye) and an antifade reagent was applied and coverslips mounted.

Identifying labels on the slides were replaced with anonymous codes before being given to an observer to count the number of chromosomes 21 per nucleus. Slides were evaluated using a Zeiss Axiophot equipped with a mercury lamp and a 63× objective. An average of 800 nuclei were analyzed per cell line.

Hybridization Probes—Biotinylated or digoxigenin-labeled chromosome 21-specific probes were either commercially obtained (Oncor) or generated using a cosmid containing a 21-specific sequence. The cosmid was labeled by nick translation with biotinylated dATP.

Calculation of Trisomy Percentages—Not all chromosomes hybridize in the FISH procedure. Therefore it was necessary to correct for the number of false trisomies caused by under-hybridization of cells that were in the G2 phase of the cell cycle and so were actually tetrasomic.

The following formula was developed to estimate the real number of trisomies present in fibroblast cultures using only the assumptions that each chromosome in a nucleus hybridizes as an independent event and all observed monosomies are actually disomies in which one chromosome failed to hybridize.

$$P = \text{probability of hybridization} = \frac{m + 2d}{2(m+d)}$$

$$T = \% \text{ real trisomies} = \frac{t}{[1-(1-P^3)]} - q\left[\frac{(1-P^4)}{[1-(1-P^4)]}\right]$$

Where M=observed % monosomies, d=observed % disomies, t=observed % trisomies, and q=observed % tetrasomies Results Table I and FIG. 2 show the percent trisomy 21 observed by FISH in fibroblast cultures of 39 Alzheimer's Disease patients and unaffected individuals. The overall average amount of trisomy 21 was 5.5% in Alzheimer's Disease cultures and 2.5% in cultures from unaffected individuals. Using the same procedure, the number of trisomies in a Down syndrome culture was determined to be 98%. The greater frequency of trisomy 21 cells in Alzheimer's Disease patients is significant (p=0.005) and is not related to the age of the affected individuals. It is unlikely that there is a general influence of time in culture on the degree of aneuploidy as this is varied in both control and Alzheimer's Disease cultures, and it has been found that human fibroblasts remain largely euploid throughout their lifetime in culture (Hayflick and Moorehead, Exp. Cell. Res. 25:585 (1961)).

Figure 3:
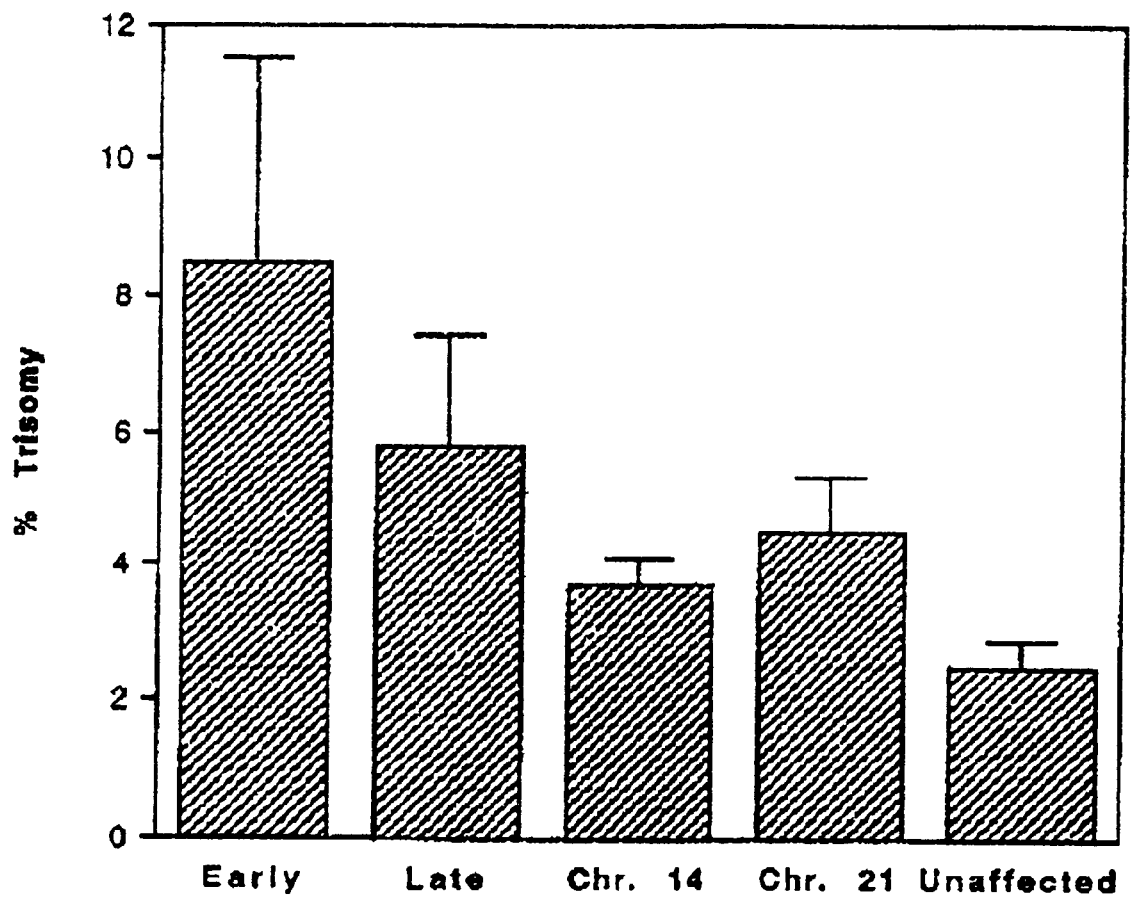
FIG. 3 is a graph showing the percentage of trisomy 21 cells in cultured fibroblasts, as determined by fluorescence in situ hybridization, for individuals with early onset of Alzheimer's Disease (before age 65 n=7), late onset of Alzheimer's Disease (after age 65 n=5), chromosome 14 linked Alzheimer's Disease (n=12), chromosome 21 linked Alzheimer's Disease (n=2) and unaffected individuals (n=13).

The Alzheimer's Disease cultures were derived from individuals with chromosome 14-linked, chromosome 21linked, early onset, or late onset disease. It is of interest to know whether the trisomies were confined only to individuals in specific categories. FIG. 3 shows that there is increased trisomy 21 in all categories of Alzheimer's Disease cultures compared to cultures from unaffected individuals. The individuals with chromosome 14-linked Alzheimer's Disease were from the large Canadian, Italian, and German pedigrees and had an average trisomy 21 frequency of 3.7t. Only two individuals with chromosome 21 linked Alzheimer's Disease were examined and they exhibited 4% and 5% trisomy 21. Individuals with early- and late-onset disease had distinctly elevated levels of trisomy 21 compared to unaffected controls. Their average trisomy 21 frequencies were 8.5% and 5.8%, respectively as compared to the unaffected individuals (2.5%). In these latter groups, insufficient family data were available to determine whether they were familial or sporadic cases of Alzheimer's Disease.

These results indicate that several different mechanisms causing Alzheimer's Disease, both familial and sporadic (which includes complex genetic and/or environmental effects), may directly induce trisomy 21 via chromosome nondisjunction. The effect of nondisjunction could be restricted to chromosome 21 alone, but more likely involves other, perhaps all, chromosomes as well. The effect of non-disjunction on other chromosomes can be determined by using the procedures described above with probes specific for the other chromosomes.

TABLE I

| Culture Name | AD Status | # of Nuclei Analyzed | % Trisomy |
|---|---|---|---|
| 0364D | AD/early | 195 | 18.9 |
| 4159 | AD/chr. 14 | 505 | 2.2 |
| 4400A | AD/early | 1481 | 1.3 |
| 4402A | AD/early | 937 | 6.7 |
| 5770 | AD/early | 517 | 4.6 |
| 5809 | AD/early | 225 | 21 |
| 5810C | AD/late | 136 | 10.5 |
| 6840B | AD/chr. 14 | 840 | 3.8 |
| 6844 | AD/chr. 14 | 1144 | 3.6 |
| 6848B | AD/chr. 14 | 1001 | 2.9 |
| 7375 | AD/early | 1115 | 4.9 |
| 7377A | AD/early | 502 | 2.2 |
| 7872 | AD/chr. 14 | 1938 | 4.7 |
| 8110 | AD/chr. 14 | 321 | 4.3 |
| 8170A | AD/chr. 14 | 1026 | 1.9 |
| 8243 | AD/late | 500 | 6.9 |
| 8245 | AD/late | 719 | 6.9 |
| 8446 | AD/chr. 14 | 1063 | 4.8 |
| 8523 | AD/chr. 14 | 614 | 5.4 |
| 8527 | AD/chr. 14 | 570 | 6.4 |
| 8563A | AD/chr. 14 | 501 | 3.3 |
| 8597 | AD/chr. 14 | 502 | 1.3 |
| 9908 | AD/late | 500 | 1.3 |
| 10788 | AD/late | 498 | 3.4 |
| CG | AD/chr. 21 | 481 | 3.7 |
| H010 | AD/chr. 21 | 479 | 5.2 |
| 8942 | Down syndrome | 1515 | 98.3 |
| 2602 | Unaffected | 853 | 3.9 |
| 4153 | Unaffected | 1017 | 2.9 |
| 7615 | Unaffected | 195 | 4.1 |
| 7865 | Unaffected | 1540 | 1.0 |
| 7871 | Unaffected | 336 | 2.1 |
| 8125 | Unaffected | 505 | 2.6 |
| 8379 | Unaffected | 508 | 3.8 |
| 8517 | Unaffected | 485 | 1.1 |
| 8620 | Unaffected | 1117 | 2.7 |
| 8701 | Unaffected | 509 | 3.9 |
| 8712 | Unaffected | 508 | 0.9 |
| 9173 | Unaffected | 612 | 0.5 |
| Swedish 2 | Unaffected | 513 | 3.4 |

Culture names are those assigned by the Coriell Cell Repository with the exception of CG and DH, which are lines from M. Benson, and Swedish 2 which is an unaffected member of a Swedish family carrying an APP mutation. Lines identified as Chr. 21 and Chr. 14 are from individuals whose Alzheimer's Disease has been linked to those chromosomes. Early and late refer to the apparent early (before age 65) and late (after age 65) age of onset of Alzheimer's Disease in individuals whose disease is either familial with no specific chromosomal linkage identified or apparently sporadic.

EXAMPLE 2
Assay for Identifying Genes Causing Chromosome Non-Disjunction

SBD8 is a yeast strain of the genotype a/α, ade2-101/ade2-101, HIS3+/−, leu2−/−, lys2−/−, trp1−/−, ura3+/−, CEN3SUP11:cen130-3:URA3 (Stoler et al.)

PRS314.GAL1-10 is a TRP1 plasmid constructed from the original pRS314 of Hieter et al., Cell, 40:381 (1985). It contains the GA/10 UAS in the RI/BAM site of the polylinker and is induced on 2% nonautoclaved galactose. The GAl1/10 UAS is repressed on 5–10% glucose.

AG09371 (GU3908) is a lymphoblastoid cell line from an affected member of a familial Alzheimer's Disease pedigree (termed FAD3, in St. George-Hyslop et al., Science, 235:885 (1987), which incorrectly identified the family as harboring a mutant gene on chromosome 21. The family has subsequently been identified as a chromosome 14 familial Alzheimer's Disease family (Schellenberg, et al., Science, 258:668 (1992); St. George-Hyslop et al., Nature Genet. 2:330 (1992)). This is a Russian-Jewish pedigree containing 23 affected individuals. The cell line AG09371 is from the NIA aging cell repository sponsored by the National Institute on Aging and located at the Coriell Institute for Medical Research in Camden, N.J. GUS3908 is the Massachusetts General Hospital cell number.

Library Construction

PolyA+ mRNA was isolated from 2×108 cells of a lymphoblastoid line (AG09371) from a familial Alzheimer's Disease patient using the FASTTRACK kit (Pharmacia). Full-length cDNA primed with oligoDT-containing primers was carried out using the SUPERSCRIPT cDNA library kit (Gibco-BRL) according to manufacturer's instructions. The resulting full-length cDNA (above 500 nucleotides in length) was ligated into the pRS314.gal1-10 vector using the BamH1 and Not1 sites to ensure directional cloning. The resulting plasmids were used to transform K-12 E. coli strain by electroporation (Potter, 1993) and plated on large (150 mm), amp-containing plates to amplify the library. DNA was prepared from the transformed bacteria by the Qiagen column method. Library DNA was used to transform SBD8 yeast cells by the lithium chloride method. Transformants were plated on plates lacking tryptophan and containing 6 μg/ml adenine at a concentration of about 500 cells/100 mm plate. Sectored colonies were visually screened by the method below, taken from Stoler et al. (1995).

Yeast Colony Screening

The mitotic segregation of SUP11-marked chromosomes bearing cen130-3 centromeres was monitored using the color colony assay on limiting adenine media (Hieter et al., 1985). SUP11 partially suppresses the red color phenotype of ade2-101 yeast cells. Hence, in a diploid yeast cell homozygous for the ade2-101 allele, one copy of SUP11 suppresses partially the red color to form homogeneous pink colonies. Two copies of SUP11 suppress fully this phenotype resulting in white colonies. Strains where SUP11 is linked genetically to a chromosome that is mitotically unstable form colonies that contain red, pink and white sectors. Red and pink sectors arise from chromosome loss (1:0) events and nondisjunction (2:0) events result in red/white sectors. Half-sectored colonies represent missegregation events that occurred at the first division after plating. The number of half-sectored colonies divided by the total number of mostly pink colonies plated represents the missegregation frequency of the SUP11-bearing chromosome. In addition, the number of red/pink and red/white half-sectored colonies is used to determine the frequency of chromosome loss or nondisjunction, respectively. The missegregation data from cen130-3 chromosomes was collected as follows. In each assay, three mostly pink colonies were picked from color media plates and about 3000 cells were spread onto large (150×15 mm) color media plates, incubated for 4 days at 30° C. and then overnight at 4° C. At least three independent assays were performed to monitor the segregation of cen130-3 chromosomes in each wild-type and cse4-1 strain.

DNA Analysis

Following multiple transformation and sector colony screening, twenty-two cDNAs were identified which continuously cause chromosome nondisjunction and sectored colonies in the transformed yeast cells. DNA prepared from twenty-two E. coli strains harboring the individual candidate human cDNA recombinant plasmids was then subjected to dideoxy sequencing analysis. Several known genes were among the candidates, including HLAB51, protein kinase C-δ, and elongation factor 1a. In addition, a number of unknown genes were identified. All sequences were mapped to their respective human chromosomes by PCR analysis of mapped YAC libraries and/or human-rodent somatic cell hybrid lines. Partial sequences are shown in FIGS. 4–26.

The plasmids isolated above containing polynucleotides corresponding to SEQ ID NOS: 6, 15, 19, 20 22, 24 and 26 were re-transfected into SBD8 yeast cells as described above. The nondisjunctive frequency for each transformation was then determined, as described above. Yeast transformed with genes corresponding to SEQ ID NOS: 6, 15, 19, 20 22, 24 and 26 showed an increase in the frequency of nondisjunction of 2.7 (standard deviation=1.92), 2.4 (standard deviation=1.74), 3.1 (standard deviation=3.17), 3.7 (standard deviation=3.21), 3.7 (standard deviation=2.1) and 3.3 (standard deviation=1.98) fold, respectively, compared with yeast transformed with the pRS314.gal1-10 vector alone.

EXAMPLE 3
AD3 and AD4/AD3LP Increase the Frequency of Chromosome Nondisjunction in cDNA Transfected Lymphoblasts The AD3 gene was obtained as described in Sherrington et al., Nature 375:754 (1995); the AD4/AD3LP gene obtained as described above. These genes were ligated into the pcDNA3 vector purchased from Invitrogen, Inc. according to procedures disclosed in "Current Protocols in Molecular Biology", John Wiley & Sons (1989) and transfected into lymphoblasts with normal karyotypes by electroporation techniques disclosed in Potter, "Methods in Enzymology: Recombinant DNA Technology," Wu ed. Orlando, Fla., Academic Press, 1993). Untransfected control cells and control cells transfected with unmodified pcDNA3 vector were also prepared. The cells were then allowed to grow for about sixty hours and the frequency of nondisjunction determined by methods disclosed in Sanchez et al., Lancet 1973:ii:269 (1973). The results are shown in Table II below:

TABLE II

CHROMOSOME NONDISJUNCTION TEST IN cDNA TRANSFECTED LYMPHOBLAST

| | $H_2O$ | | |
|---|---|---|---|
| Expt# | Count* | Total No. of Cells | Count/Tot |
| 1 | 2 | 20 | 0.10 |
| 2 | 0 | 17 | 0.00 |
| 3 | 4 | 25 | 0.16 |

TABLE II-continued

CHROMOSOME NONDISJUNCTION TEST IN cDNA TRANSFECTED LYMPHOBLAST

| | pcDNA3 | | | |
|---|---|---|---|---|
| | Count* | Total No. of Cells | Count/Tot | Ratio to $H_2O$ |
| 1 | 0 | 20 | 0.00 | 0.00 |
| 2 | | | | |
| 3 | 2 | 24 | 0.08 | 0.52 |

*Total number of aneuploid cells or cells with broken or translocated chromosomes.

Cells transfected with the AD3 gene or the AD4/AD3LP gene were found to have an increased frequency of nondisjunction compared with control cells.

EXAMPLE 4

Determination of the Entire Polynucleotide and Amino Acid Sequence of AD4/AD3LP

Identification of T03796 and Cloning of the Full-Length cDNA—All nucleotide sequences in the GenBank data base were translated into amino acid sequences in all six reading frames and then compared to the published protein sequence (24) of AD3 (S182), by using TBLASTIN (National Center for Biotechnology Information server). The expressed sequence tag (EST) sequence (T03796) whose encoded protein was most highly homologous to AD3 was thus identified, and the corresponding cDNA clone was obtained from the Lawrence Livermore National Laboratory (IMAGE Consortium). After we had determined the full sequence of T03796 (see below), additional EST sequences identical to T03796 (GenBank accession nos. R16831 and R05822) were also identified. Because all of these EST clones were partial, 5' rapid amplification of cDNA ends (RACE) was used to complete the full-length cDNA corresponding to T03796.

Sequencing and Analysis of DNA and Encoded Proteins—The T03796 sequence in GenBank consists of 476 nt, with some errors. We resequenced the reported region and then sequenced the rest of T03796 and the 5' RACE clones for a total of 2.4 kb. DNA sequencing was carried out by the dideoxynucleotide china-terminating procedure with fluorescent-tag-labeled deoxynucleotides by the Biopolymer Laboratory, Harvard Medical School. Oligonucleotide primers used for sequencing were also synthesized by the Biopolymer Laboratory. Sequences were compared for homology to other sequences in the GenBank, GenEMBL, and dbest data bases, by using FASTA (GCG software package from the Wisconsin Genetics Computer Group) and by BLASTIN and BLASTIN (National Center for Biotechnology Information server).

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. A method of identifying an agent which is an inhibitor of improper chromosome segregation comprising the steps of:
   a) providing cells, referred to as tester cells, transfected with a plasmid suitable for reproduction in the tester cells, wherein the plasmid comprises a gene, referred to as a test gene, whose gene product causes chromosome missegregation and the appropriate control elements for expressing or over expressing the gene;
   b) exposing the tester cells to an agent being tested as an inhibitor of chromosome missegregation;
   c) incubating the tester cells under conditions suitable for the tester cells to reproduce, thereby producing progeny cells;
   d) assessing the number of aneuploid progeny cells or the number of progeny cells with a chromosome having a break or a translocation, wherein a lower frequency of aneuploid progeny cells or a lower frequency of progeny cells with a chromosome having a break or a translocation in the presence of the agent being tested than in the absence of the agent being tested is indicative that the agent is an inhibitor of improper chromosome segregation.

2. The method of claim 1 wherein the tester cells are mammalian cells.

3. The method of claim 2 wherein the mammalian cells are human cells.

4. The method of claim 1 wherein:
   a) the tester cells comprise:
      i) a chromosome with a mutated centromere which makes the chromosome prone to improper segregation; and
      ii) a gene on the chromosome with the mutated centromere, referred to as a marker gene, whose gene product gives a quantifiable indication of the number of chromosomes with the mutated centromere present in the tester cell;
   b) the number of aneuploid progeny cells is determined by quantifying the indication given by the marker gene product; and
   c) the tester cells are yeast cells.

5. The method of claim 4 wherein the marker gene encodes a gene product which enhances or suppresses the expression of a second marker gene, wherein the second marker gene encodes a gene product which gives a quantifiable indication of the number of chromosomes with the mutated centromere present in the test cell.

6. The method of claim 4 wherein the chromosome of (a)(i) comprises two marker genes, wherein the first marker gene is sup 11 and the second marker gene is ade2.

7. The method of claim 1 wherein the test gene comprises a polynucleotide represented by SEQ ID NO: 1, or a polynucleotide which comprises at least 90 nucleotides and is contained in the test gene.

8. The method of claim 1 wherein the test gene comprises a polydeoxynucleotide represented by SEQ ID NO: 3, or a polydeoxynucleotide which comprises at least 90 nucleotides and is contained in the test gene.

9. The method of claim 1 wherein the test gene comprises a polydeoxynucleotide represented by SEQ ID NO: 27, or a polydeoxynucleotide which comprises at least 90 nucleotides and is contained in the test gene.

10. The method of claim 1 wherein the test gene comprises a polydeoxynucleotide represented by a SEQ ID NO selected from the group consisting of: SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and polydeoxynucleotides which comprise at least 90 nucleotides and are contained in the test gene.

11. The method of claim 2 wherein the test gene encodes an Apolipoprotein E.

12. The method of claim 1 wherein the test gene comprises a polydeoxynucleotide represented by a SEQ ID NO selected from the group consisting of: SEQ ID NO: 5, SEQ ID NO: 6, SEQ ID NO: 7, SEQ ID NO: 8, SEQ ID NO: 9, SEQ ID NO: 10, SEQ ID NO: 11, SEQ BD NO: 12, SEQ ID NO: 13, and SEQ ID NO: 14.

* * * * *

UNITED STATES PATENT AND TRADEMARK OFFICE
CERTIFICATE OF CORRECTION

PATENT NO. : 5,985,564
DATED : November 16, 1999
INVENTOR(S) : Huntington Potter and Jinhe Li It is certified that error appears in the above-identified patent and that said Letters Patent is hereby corrected as shown below:

At Col. 1, before the Background of the Invention section, insert the following:

--GOVERNMENT FUNDING
This invention was supported by NIH Grant Nos. AG09665 and AG08084. The government has certain rights in this invention.--

Signed and Sealed this

Twelfth Day of September, 2000

Attest:

Q. TODD DICKINSON

*Attesting Officer*            *Director of Patents and Trademarks*